(12) United States Patent
Thapliyal et al.

(10) Patent No.: US 9,033,885 B2
(45) Date of Patent: *May 19, 2015

(54) SYSTEM AND METHOD FOR ENERGY DELIVERY TO TISSUE WHILE MONITORING POSITION, LESION DEPTH, AND WALL MOTION

(75) Inventors: Hira V. Thapliyal, Los Altos, CA (US); David A. Gallup, Alameda, CA (US); James W. Arenson, Woodside, CA (US)

(73) Assignee: VYTRONUS, INC., Sunnyvale, CA (US)

(*) Notice: Subject to any disclaimer, the term of this patent is extended or adjusted under 35 U.S.C. 154(b) by 233 days.

This patent is subject to a terminal disclaimer.

(21) Appl. No.: 12/609,759

(22) Filed: Oct. 30, 2009

(65) Prior Publication Data

US 2010/0113985 A1 May 6, 2010

Related U.S. Application Data

(60) Provisional application No. 61/109,873, filed on Oct. 30, 2008, provisional application No. 61/109,875, filed on Oct. 30, 2008, provisional application No. 61/109,879, filed on Oct. 30, 2008.

(51) Int. Cl.
*A61B 8/00* (2006.01)
*A61N 7/00* (2006.01)
(Continued)

(52) U.S. Cl.
CPC ............ *A61N 7/00* (2013.01); *A61N 2007/0052* (2013.01); *A61B 8/12* (2013.01);
(Continued)

(58) Field of Classification Search
USPC .............. 601/2; 600/407, 411, 427, 439, 508; 604/22; 606/27–40; 607/2, 96–102, 607/115–132
See application file for complete search history.

(56) References Cited

U.S. PATENT DOCUMENTS 4,641,649 A  2/1987  Walinsky et al.
4,757,820 A  7/1988  Itoh
(Continued)

FOREIGN PATENT DOCUMENTS

DE  10037660  2/2002
WO  WO 99/02096  1/1999
(Continued)

OTHER PUBLICATIONS

Pappone et al. Non-fluoroscopic mapping as a guide for atrial ablation: current status and expectations for the future. European Heart Journal Supplements 9:1136-1147. Dec. 2007.*

(Continued)

*Primary Examiner* — Parikha Mehta
(74) *Attorney, Agent, or Firm* — Wilson Sonsini Goodrich & Rosati

(57) ABSTRACT

Systems and methods for ablating tissue include an ablation device having an energy source and a sensor. The energy source provides a beam of energy directable to target tissue, and the sensor senses energy reflected back from the target tissue. The sensor collects various information from the target tissue in order to facilitate adjustment of ablation operating parameters, such as changing power or position of the energy beam. Gap distance between the energy source and target tissue, energy beam incident angle, tissue motion, tissue type, lesion depth, etc. are examples of some of the information that may be collected during the ablation process and used to help control ablation of the tissue.

16 Claims, 10 Drawing Sheets

(51) Int. Cl.
*A61B 8/12* (2006.01)
*A61N 7/02* (2006.01)
*A61B 17/00* (2006.01)
*A61B 18/00* (2006.01)
*A61B 19/00* (2006.01)

(52) U.S. Cl.
CPC ........... *A61B2017/00084* (2013.01); *A61B 2017/00092* (2013.01); *A61B 2017/00106* (2013.01); *A61B 2018/00029* (2013.01); *A61B 2018/00642* (2013.01); *A61B 2019/461* (2013.01); *A61N 7/022* (2013.01); *A61N 2007/0073* (2013.01); *A61N 2007/0078* (2013.01)

(56) References Cited

U.S. PATENT DOCUMENTS

| | | | |
|---|---|---|---|
| 5,164,920 A | 11/1992 | Bast et al. | |
| 5,246,438 A | 9/1993 | Langberg | |
| 5,295,484 A | 3/1994 | Marcus et al. | |
| 5,314,466 A | 5/1994 | Stern et al. | |
| 5,405,346 A | 4/1995 | Grundy et al. | |
| 5,471,988 A | 12/1995 | Fujio et al. | |
| 5,588,432 A | 12/1996 | Crowley | |
| 5,718,241 A | 2/1998 | Ben-Haim et al. | |
| 5,735,811 A | 4/1998 | Brisken | |
| 6,012,457 A | 1/2000 | Lesh | |
| 6,024,740 A | 2/2000 | Lesh et al. | |
| 6,052,576 A | 4/2000 | Lambourg | |
| 6,064,902 A | 5/2000 | Haissaguerre et al. | |
| 6,117,101 A | 9/2000 | Diederich et al. | |
| 6,161,543 A | 12/2000 | Cox et al. | |
| 6,164,283 A | 12/2000 | Lesh | |
| 6,237,605 B1 | 5/2001 | Vaska et al. | |
| 6,245,064 B1 | 6/2001 | Lesh et al. | |
| 6,245,095 B1 | 6/2001 | Dobak, III et al. | |
| 6,251,129 B1 | 6/2001 | Dobak, III et al. | |
| 6,251,130 B1 | 6/2001 | Dobak, III et al. | |
| 6,254,599 B1 | 7/2001 | Lesh et al. | |
| 6,261,312 B1 | 7/2001 | Dobak, III et al. | |
| 6,267,734 B1 * | 7/2001 | Ishibashi et al. | 601/2 |
| 6,277,116 B1 | 8/2001 | Utely et al. | |
| 6,305,378 B1 | 10/2001 | Lesh | |
| 6,311,090 B1 | 10/2001 | Knowlton | |
| 6,311,692 B1 | 11/2001 | Vaska et al. | |
| 6,314,962 B1 | 11/2001 | Vaska et al. | |
| 6,314,963 B1 | 11/2001 | Vaska et al. | |
| 6,379,378 B1 | 4/2002 | Werneth et al. | |
| 6,383,151 B1 | 5/2002 | Diederich et al. | |
| 6,387,089 B1 | 5/2002 | Kreindel et al. | |
| 6,416,511 B1 | 7/2002 | Lesh et al. | |
| 6,468,296 B1 | 10/2002 | Dobak, III et al. | |
| 6,474,340 B1 | 11/2002 | Vaska et al. | |
| 6,475,231 B2 | 11/2002 | Dobak, III et al. | |
| 6,478,811 B1 | 11/2002 | Dobak, III et al. | |
| 6,478,812 B2 | 11/2002 | Dobak, III et al. | |
| 6,484,727 B1 | 11/2002 | Vaska et al. | |
| 6,491,039 B1 | 12/2002 | Dobak, III | |
| 6,491,716 B2 | 12/2002 | Dobak, III et al. | |
| 6,500,121 B1 | 12/2002 | Slayton et al. | |
| 6,500,174 B1 | 12/2002 | Maguire et al. | |
| 6,502,576 B1 | 1/2003 | Lesh | |
| 6,514,244 B2 | 2/2003 | Pope et al. | |
| 6,514,249 B1 | 2/2003 | Maguire et al. | |
| 6,517,536 B2 | 2/2003 | Hooven et al. | |
| 6,529,756 B1 | 3/2003 | Phan et al. | |
| 6,533,804 B2 | 3/2003 | Dobak, III et al. | |
| 6,540,771 B2 | 4/2003 | Dobak, III et al. | |
| 6,542,781 B1 | 4/2003 | Koblish et al. | |
| 6,546,935 B2 | 4/2003 | Hooven | |
| 6,547,788 B1 | 4/2003 | Maguire et al. | |
| 6,551,349 B2 | 4/2003 | Lasheras et al. | |
| 6,576,001 B2 | 6/2003 | Werneth et al. | |
| 6,585,752 B2 | 7/2003 | Dobak, III et al. | |
| 6,592,576 B2 | 7/2003 | Andrews et al. | |
| 6,595,989 B1 | 7/2003 | Schaer | |
| 6,599,288 B2 | 7/2003 | Maguire et al. | |
| 6,602,276 B2 | 8/2003 | Dobak, III et al. | |
| 6,605,084 B2 | 8/2003 | Acker et al. | |
| 6,607,502 B1 | 8/2003 | Maguire et al. | |
| 6,607,527 B1 | 8/2003 | Ruiz et al. | |
| 6,613,046 B1 | 9/2003 | Jenkins et al. | |
| 6,635,054 B2 | 10/2003 | Fjield et al. | |
| 6,645,199 B1 | 11/2003 | Jenkins et al. | |
| 6,645,202 B1 | 11/2003 | Pless et al. | |
| 6,648,908 B2 | 11/2003 | Dobak, III et al. | |
| 6,652,515 B1 | 11/2003 | Maguire et al. | |
| 6,652,517 B1 | 11/2003 | Hall et al. | |
| 6,666,614 B2 | 12/2003 | Fechter et al. | |
| 6,666,858 B2 | 12/2003 | Lafontaine | |
| 6,669,655 B1 | 12/2003 | Acker et al. | |
| 6,669,687 B1 | 12/2003 | Saadat | |
| 6,676,688 B2 | 1/2004 | Dobak, III et al. | |
| 6,676,689 B2 | 1/2004 | Dobak, III et al. | |
| 6,676,690 B2 | 1/2004 | Werneth | |
| 6,685,732 B2 | 2/2004 | Kramer | |
| 6,689,128 B2 | 2/2004 | Sliwa, Jr. et al. | |
| 6,692,488 B2 | 2/2004 | Dobak, III et al. | |
| 6,695,873 B2 | 2/2004 | Dobak, III et al. | |
| 6,701,931 B2 | 3/2004 | Sliwa, Jr. et al. | |
| 6,702,842 B2 | 3/2004 | Dobak, III et al. | |
| 6,711,444 B2 | 3/2004 | Koblish | |
| 6,719,755 B2 | 4/2004 | Sliwa, Jr. et al. | |
| 6,745,080 B2 | 6/2004 | Koblish | |
| 6,752,805 B2 | 6/2004 | Maguire et al. | |
| 6,758,847 B2 | 7/2004 | Maguire | |
| 6,763,722 B2 | 7/2004 | Fjield et al. | |
| 6,780,183 B2 | 8/2004 | Jimenez, Jr. et al. | |
| 6,786,218 B2 | 9/2004 | Dobak, III | |
| 6,805,128 B1 | 10/2004 | Pless et al. | |
| 6,805,129 B1 | 10/2004 | Pless et al. | |
| 6,814,733 B2 | 11/2004 | Schwartz et al. | |
| 6,840,936 B2 | 1/2005 | Sliwa, Jr. et al. | |
| 6,858,026 B2 | 2/2005 | Sliwa, Jr. et al. | |
| 6,869,431 B2 | 3/2005 | Maguire et al. | |
| 6,872,205 B2 | 3/2005 | Lesh et al. | |
| 6,889,694 B2 | 5/2005 | Hooven | |
| 6,893,438 B2 | 5/2005 | Hall et al. | |
| 6,896,673 B2 | 5/2005 | Hooven | |
| 6,899,710 B2 | 5/2005 | Hooven | |
| 6,899,711 B2 | 5/2005 | Stewart et al. | |
| 6,904,303 B2 | 6/2005 | Phan et al. | |
| 6,905,494 B2 | 6/2005 | Yon et al. | |
| 6,905,498 B2 | 6/2005 | Hooven | |
| 6,905,509 B2 | 6/2005 | Dobak, III et al. | |
| 6,908,464 B2 | 6/2005 | Jenkins et al. | |
| 6,920,883 B2 | 7/2005 | Bessette et al. | |
| 6,923,806 B2 | 8/2005 | Hooven et al. | |
| 6,923,808 B2 | 8/2005 | Taimisto | |
| 6,929,639 B2 | 8/2005 | Lafontaine | |
| 6,932,811 B2 | 8/2005 | Hooven et al. | |
| 6,949,095 B2 | 9/2005 | Vaska et al. | |
| 6,949,097 B2 | 9/2005 | Stewart et al. | |
| 6,953,460 B2 | 10/2005 | Maguire et al. | |
| 6,954,977 B2 | 10/2005 | Maguire et al. | |
| 6,955,173 B2 | 10/2005 | Lesh | |
| 6,964,660 B2 | 11/2005 | Maguire et al. | |
| 6,966,908 B2 | 11/2005 | Maguire et al. | |
| 6,971,394 B2 | 12/2005 | Sliwa, Jr. et al. | |
| 6,974,454 B2 | 12/2005 | Hooven | |
| 6,984,233 B2 | 1/2006 | Hooven | |
| 6,997,925 B2 | 2/2006 | Maguire et al. | |
| 7,001,378 B2 | 2/2006 | Yon et al. | |
| 7,001,415 B2 | 2/2006 | Hooven | |
| 7,044,135 B2 | 5/2006 | Lesh | |
| 7,063,682 B1 | 6/2006 | Whayne et al. | |
| 7,142,905 B2 | 11/2006 | Slayton et al. | |
| 7,275,450 B2 | 10/2007 | Hirai et al. | |
| 7,282,060 B2 * | 10/2007 | DeBenedictis et al. | 607/88 |
| 7,285,116 B2 | 10/2007 | de la Rama et al. | |
| 7,306,593 B2 | 12/2007 | Keidar et al. | |
| 7,393,325 B2 | 7/2008 | Barthe et al. | |
| 2002/0087151 A1 | 7/2002 | Mody et al. | |

(56) References Cited

U.S. PATENT DOCUMENTS

| | | | |
|---|---|---|---|
| 2003/0050630 A1 | 3/2003 | Mody et al. | |
| 2003/0050631 A1 | 3/2003 | Mody et al. | |
| 2005/0049582 A1 | 3/2005 | DeBenedictis et al. | |
| 2005/0165388 A1 | 7/2005 | Bhola | |
| 2005/0256518 A1* | 11/2005 | Rama et al. | 606/27 |
| 2005/0267453 A1 | 12/2005 | Wong et al. | |
| 2006/0122508 A1 | 6/2006 | Slayton et al. | |
| 2006/0135953 A1* | 6/2006 | Kania et al. | 606/21 |
| 2007/0027445 A1 | 2/2007 | Gifford et al. | |
| 2007/0265609 A1 | 11/2007 | Thapliyal et al. | |
| 2007/0265610 A1 | 11/2007 | Thapliyal et al. | |
| 2008/0039746 A1 | 2/2008 | Hissong et al. | |
| 2008/0077200 A1 | 3/2008 | Bendett et al. | |
| 2009/0312673 A1 | 12/2009 | Thapliyal et al. | |
| 2009/0312693 A1 | 12/2009 | Thapliyal et al. | |
| 2009/0312755 A1 | 12/2009 | Thapliyal et al. | |
| 2010/0016762 A1 | 1/2010 | Thapliyal et al. | |
| 2010/0049099 A1 | 2/2010 | Thapliyal et al. | |
| 2013/0096593 A1 | 4/2013 | Thapliyal et al. | |
| 2014/0324085 A1 | 10/2014 | Thapliyal et al. | |

FOREIGN PATENT DOCUMENTS

| | | |
|---|---|---|
| WO | WO 2005/117734 | 12/2005 |
| WO | WO 2006/034000 A1 | 3/2006 |

OTHER PUBLICATIONS

"A new treatment for atrial fibrillation?" Medical Device & Diagnostic Industry, Feb. 2006, p. 30; retrieved from the Internet: <<http://www.devicelink.com/mddi/archive/06/02/013.html>>, 2 pages total.

Bushberg et al., *The Essential Physics of Medical Imaging*, 2nd edition, Lippincott Williams & Wilkins 2002, p. 491.

Cox et al. "Current status of the Maze procedure for the treatment of atrial fibrillation," Semin Thorac Cardiovasc Surg. Jan. 2000;12(1):15-9.

Cox et al., "Electrophysiologic basis, surgical development, and clinical results of the maze procedure for atrial flutter and atrial fibrillation," Adv Card Surg. 1995;6:1-67.

Cox et al., "Modification of the maze procedure for atrial flutter and atrial fibrillation. II, Surgical technique of the maze III procedure," J Thorac Cardiovasc Surg. Aug. 1995;110(2):485-95.

Cox et al., "The development of the Maze procedure for the treatment of atrial fibrillation," Semin Thorac Cardiovasc Surg. Jan. 2000;12(1):2-14.

Gentry et al., "Integrated Catheter for 3-D Intracardiac Echocardiography and Ultrasound Ablation," IEEE Transactions on Ultrasonics, Ferroelectrics, and Frequency Control, vol. 51, No. 7, pp. 799-807.

Gill, "How to perform pulmonary vein isolation," Europace, 2004; 6 (2): 83-91; retrieved from the Internet: <<http://europace.oxfordjournals.org/cgi/reprint/6/2/83>>.

Gillinov et al., Atrial fibrillation: current surgical options and their assessment,: Annals of Thoracic Surgery 2002; 74:2210-7; retrieved from the Internet: <<http://ats.ctsnetjournals.org/cgi/reprint/74/6/2210>>.

Haissaguerre et al., "Spontaneous Initiation of Atrial Fibrillation by Ectopic Beats Originating in the Pulmonary Veins," New England J Med., Sep. 3, 1998; 339(10):659-666; retrieved from the Internet: <<http://content.nejm.org/cgi/reprint/339/10/659.pdf>>.

Levinson, "Endocardial Microwave Ablation: A New Surgical Approach for Atrial Fibrillation"; The Heart Surgery Forum, 2006.

Maessen et al., "Beating heart surgical treatment of atrial fibrillation with microwave ablation," Ann Thorac Surg 2002;74:S1307-S1311; retrieved from the Internet: <<http://ats.ctsnetjournals.org/cgi/reprint/74/4/S1307>>.

Nathan et al., "The junction between the left atrium and the pulmonary veins, An anatomic study of human hearts," Circulation 1966; 34:412-422; retrieved from the Internet: <<http://circ.ahajournals.org/cgi/reprint/34/3/412>>.

Sueda et al., "Efficacy of a simple left atrial procedure for chronic atrial fibrillation in mitral valve operations," Ann Thorac Surg 1997; 63:1070-1075.

Sueda et al., "Simple left atrial procedure for chronic atrial fibrillation associated with mitral valve disease," Ann Thorac Surg 1996; 62: 1796-1800.

Ter Haar, "Acoustic Surgery", Physics Today, 2001; 54(12):29-34.

U.S. Appl. No. 12/483,174, filed Jun. 11, 2009; first named inventor: Hira V. Thapliyal.

U.S. Appl. No. 13/630,697, filed Sep. 28, 2012, Thapliyal et al.

Office action dated Aug. 21, 2013 for U.S. Appl. No. 12/630,697.

U.S. Appl. No. 14/177,194, filed Feb. 10, 2014, Ismagilov et al.

Office action dated Jan. 14, 2014 for U.S. Appl. No. 13/630,697.

Office action dated Jan. 22, 2015 for U.S. Appl. No. 14/330,422.

\* cited by examiner

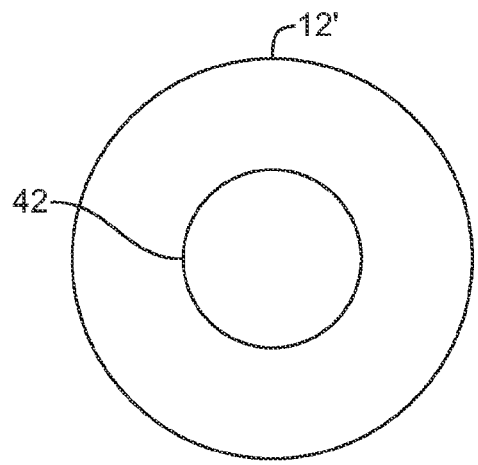
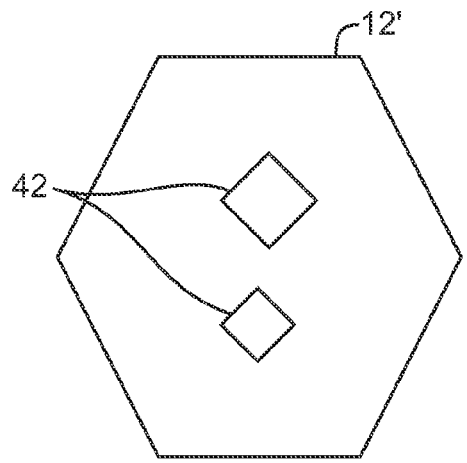
FIG. 4A   FIG. 4B
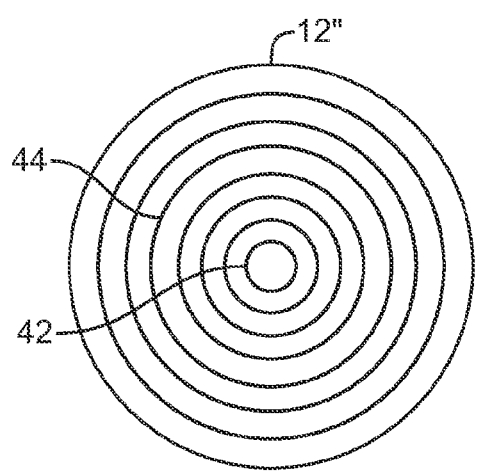
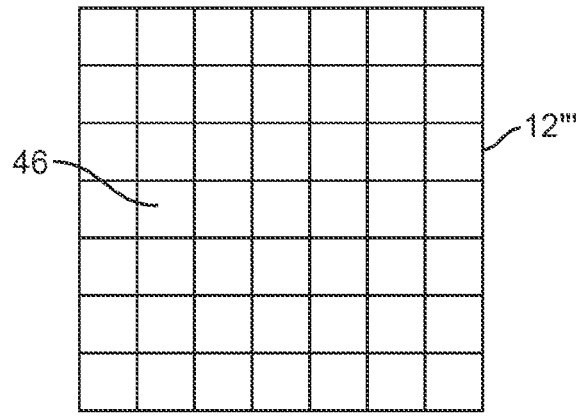
FIG. 5   FIG. 6

SYSTEM AND METHOD FOR ENERGY DELIVERY TO TISSUE WHILE MONITORING POSITION, LESION DEPTH, AND WALL MOTION

CROSS-REFERENCES TO RELATED APPLICATIONS

The present application is a non-provisional of, and claims the benefit of priority of U.S. Provisional Patent Application Nos. 61/109,873 filed Oct. 30, 2008; 61/109,875 filed Oct. 30, 2008; and 61/109,879 filed Oct. 30, 2008; the entire contents of which are incorporated herein by reference.

The present application is also related to U.S. Provisional Patent Application Nos. 61/110,905; 61/115,403; 61/148,809; 61/109,973; 61/109,875; 61/109,879; 61/109,881; 61/109,882; 61/109,889; 61/109,893; 61/254,997; and U.S. patent application Ser. Nos. 11/747,862 (now U.S. Pat. No. 7,950,397); 11/747,867 (now U.S. Pat. No. 7,942,871); 12/480,929 (now pending U.S. Patent Publication No. 2009/0312755); 12/480,256 (now abandoned U.S. Patent Publication No. 2009/0312693); 12/483,174 (now abandoned U.S. Patent Publication No. 2010/0152582); 12/482,640 (now pending U.S. Patent Publication No. 2010/0312673); 12/505,326 (now pending U.S. Patent Publication No. 2010/0049099); 12/505,335; (now pending U.S. Patent Publication No. 2010/0016762); the entire contents of which are incorporated herein by reference.

BACKGROUND OF THE INVENTION

1. Field of the Invention

The present application generally relates to systems and methods for ablating tissue. More specifically, the present application relates to the treatment of fibrillation or other arrhythmias of the heart by using ultrasound energy, and even more specifically, the present application relates to ablation systems and methods used to treat atrial fibrillation that provide information related to position of the ablation device relative to the tissue, as well as providing information about depth of the lesion and motion of the energy source relative to the tissue.

The condition of atrial fibrillation (AF) is characterized by the abnormal (usually very rapid) beating of the left atrium of the heart which is out of synch with the normal synchronous movement ('normal sinus rhythm') of the heart muscle. In normal sinus rhythm, the electrical impulses originate in the sino-atrial node ('SA node') which resides in the right atrium. The abnormal beating of the atrial heart muscle is known as 'fibrillation' and is caused by electrical impulses originating instead at points other than the SA node, for example, in the pulmonary veins (PV).

There are pharmacological treatments for this condition with varying degree of success. In addition, there are surgical interventions aimed at removing the aberrant electrical pathways from PV to the left atrium ('LA') such as the 'Cox-Maze III Procedure'. This procedure has been shown to be 99% effective but requires special surgical skills and is time consuming. Thus, there has been considerable effort to copy the Cox-Maze procedure using a less invasive percutaneous catheter-based approach. Less invasive treatments have been developed which involve use of some form of energy to ablate (or kill) the tissue surrounding the aberrant focal point where the abnormal signals originate in PV. The most common methodology is the use of radio-frequency ('RF') electrical energy to heat the muscle tissue and thereby ablate it. The aberrant electrical impulses are then prevented from traveling from PV to the atrium (achieving the 'conduction block') and thus avoiding the fibrillation of the atrial muscle. Other energy sources, such as microwave, laser, and ultrasound have been utilized to achieve the conduction block. In addition, techniques such as cryoablation, administration of ethanol, and the like have also been used.

More recent approaches for the treatment of AF involve the use of ultrasound energy. The target tissue of the region surrounding the pulmonary vein is heated with ultrasound energy emitted by one or more ultrasound transducers.

When delivering energy to tissue, in particular when ablating tissue with ultrasound to treat atrial-fibrillation, a substantially transmural lesion (burning all the way through the tissue) must be made to form a proper conduction block. Achieving a substantially transmural lesion though has many challenges. For example, the physician must insure proper alignment of the energy-delivering device relative to the target tissue. If the energy source is too far away from the tissue, the energy reaching the tissue will be insufficient to create a substantially transmural lesion. If the energy source is too close, the energy may damage the tissue or cause the energy source to overheat. Thus, there is a need for systems and methods that can account for the position of an energy delivery device during ablation of tissue. Moreover, successful ablation is dependent on proper positioning of the ablation device. Because the target tissue can move during ablation (e.g. when ablating tissue in a beating heart), it can also be difficult to create a lesion having the desired depth in the tissue. Additionally the motion of the tissue can result in damage of the tissue, insufficient ablation of the tissue, or damage to the device. Thus there is also a need for improved systems and methods that can accommodate tissue motion during ablation and that can provide information about the depth of the lesion. It would also be desirable to provide an ablation system that is easy to use, easy to manufacture and that is lower in cost than current commercial systems. At least some of these objectives will be met by the disclosure provided herein.

2. Description of Background Art

Patents related to the treatment of atrial fibrillation include, but are not limited to the following: U.S. Pat. Nos. 6,997,925; 6,996,908; 6,966,908; 6,964,660; 6,955,173; 6,954,977; 6,953,460; 6,949,097; 6,929,639; 6,872,205; 6,814,733; 6,780,183; 6,666,858; 6,652,515; 6,635,054; 6,605,084; 6,547,788; 6,514,249; 6,502,576; 6,416,511; 6,383,151; 6,305,378; 6,254,599; 6,245,064; 6,164,283; 6,161,543; 6,117,101; 6,064,902; 6,052,576; 6,024,740; 6,012,457; 5,405,346; 5,314,466; 5,295,484; 5,246,438; and 4,641,649.

Patent Publications related to the treatment of atrial fibrillation include, but are not limited to International PCT Publication No. WO 99/02096; and U.S. Patent Publication No. 2005/0267453.

Scientific publications related to the treatment of atrial fibrillation include, but are not limited to: Haissaguerre, M. et al., *Spontaneous Initiation of Atrial Fibrillation by Ectopic Beats Originating in the Pulmonary Veins*, New England J Med., Vol. 339:659-666; J. L. Cox et al., *The Development of the Maze Procedure for the Treatment of Atrial Fibrillation*, Seminars in Thoracic & Cardiovascular Surgery, 2000; 12: 2-14; J. L. Cox et al., *Electrophysiologic Basis, Surgical Development, and Clinical Results of the Maze Procedure for Atrial Flutter and Atrial Fibrillation*, Advances in Cardiac Surgery, 1995; 6: 1-67; J. L. Cox et al., *Modification of the Maze Procedure for Atrial Flutter and Atrial Fibrillation. II, Surgical Technique of the Maze III Procedure*, Journal of Thoracic & Cardiovascular Surgery, 1995;110:485-95; J. L. Cox, N. Ad, T. Palazzo, et al. *Current Status of the Maze*

*Procedure for the Treatment of Atrial Fibrillation*, Seminars in Thoracic & Cardiovascular Surgery, 2000; 12: 15-19; M. Levinson, *Endocardial Microwave Ablation: A New Surgical Approach for Atrial Fibrillation*; The Heart Surgery Forum, 2006; Maessen et al., *Beating Heart Surgical Treatment of Atrial Fibrillation with Microwave Ablation*, Ann Thorac Surg 74: 1160-8, 2002; A. M. Gillinov, E. H. Blackstone and P. M. McCarthy, *Atrial Fibrillation: Current Surgical Options and their Assessment*, Annals of Thoracic Surgery 2002;74:2210-7; Sueda T., Nagata H., Orihashi K., et al., *Efficacy of a Simple Left Atrial Procedure for Chronic Atrial Fibrillation in Mitral Valve Operations*, Ann Thorac Surg 1997;63:1070-1075; Sueda T., Nagata H., Shikata H., et al.; *Simple Left Atrial Procedure for Chronic Atrial Fibrillation Associated with Mitral Valve Disease*, Ann Thorac Surg 1996; 62:1796-1800; Nathan H., Eliakim M., *The Junction Between the Left Atrium and the Pulmonary Veins, An Anatomic Study of Human Hearts*, Circulation 1966;34:412-422; Cox J. L., Schuessler R. B., Boineau J. P., *The Development of the Maze Procedure for the Treatment of Atrial Fibrillation*, Semin Thorac Cardiovasc Surg 2000;12:2-14; and Gentry et al., *Integrated Catheter for 3-D Intracardiac Echocardiography and Ultrasound Ablation*, IEEE Transactions on Ultrasonics, Ferroelectrics, and Frequency Control, Vol. 51, No. 7, pp 799-807.

BRIEF SUMMARY OF THE INVENTION

The present application generally relates to systems and methods for ablating tissue. More specifically, the present application relates to the treatment of fibrillation or other arrhythmias of the heart by using ultrasound energy, and even more specifically, the present application relates to ablation systems and methods used to treat atrial fibrillation that provide information related to position of the ablation device relative to the tissue, as well as providing information about depth of the lesion and motion of the energy source relative to the tissue.

In a first aspect of the present invention, a method of ablating tissue in a patient as a treatment for fibrillation comprises providing an ablation device having an energy source and a sensor. The energy source provides a beam of energy directable to target tissue, and the sensor senses energy reflected back from the target tissue. The sensor collects a noise profile of the ablation device. The ablation device is positioned adjacent the target tissue, and an amplitude mode data set that characterizes the target tissue is collected with the sensor. The noise profile is removed from the amplitude mode data set to determine a gap distance between the energy source and the target tissue. The target tissue is ablated with the beam of energy and operating parameters of the ablating step are adjusted in response to the gap distance.

In any aspect of the present invention, the energy source may comprise an ultrasound transducer. Positioning of the ablation device may comprise advancing the ablation device into a left atrium of the heart. The ablating may create a contiguous lesion in the target tissue, and the lesion may block aberrant electrical pathways in the tissue so as to reduce or eliminate the fibrillation. The fibrillation may comprise atrial fibrillation.

The noise profile may comprise an average amplitude value from a set of samples obtained in an echo-less environment. The noise profile may also comprise one of a signal pattern, a frequency band, and a set of signals. The noise profile may comprise electrical noise, backscatter noise of a fluid, or sensor noise. Collecting the noise profile may comprise positioning at least a portion of the ablation device into a fluid and collecting samples, or collection may be performed during calibration of the ablation device. Collecting of the noise profile may further comprise storing the noise profile data.

The amplitude mode data set may be collected continuously or periodically during the ablating, or during a during a diagnostic sweep of the target tissue prior to the ablating. Removing the noise may be repeated continuously or periodically during the ablating.

The method may further comprise using a plurality of gap distances to approximate an incident angle of the beam of energy relative to a surface of the target tissue. Operating parameters of the ablation step may be adjusted in response to the approximated incident angle. The adjusting may comprise adjusting the power in the beam of energy, or repositioning the energy source relative to the target tissue.

In another aspect of the present invention, a method of ablating tissue in a patient as a treatment for fibrillation comprises providing an ablation device having an energy source and a sensor. The energy source provides a beam of energy directable to target tissue, and the sensor senses energy reflected back from the target tissue. The ablation device is positioned adjacent the target tissue, and data is collected over a surface of the target tissue with the sensor. A map of the tissue is generated and the target tissue is ablated with the beam of energy. The tissue map is used to facilitate execution of the ablation step.

The collecting step may comprise moving the sensor across the target tissue in any pattern, including a zig-zag pattern or a continuous path. Collecting the data may comprise collecting gap distance between the energy source and a surface of the target tissue.

The map may be generated as a part of a diagnostic sweep of the target tissue prior to the ablating step, and the map may indentify anatomical structure in the target tissue such as the pulmonary veins. The map may indicate gap distance between the energy source and a surface of the target tissue, or the map may indicate surface contours and angles of the target tissue. The map may comprise a two dimensional or a three dimensional representation of the target tissue.

Use of the tissue map may facilitate generation of an ablation path or adjustment of power in the beam of energy. The map may also facilitate planning of ablation path distances. The map may comprise angles of the energy beam relative to the target tissue, and use of the map may facilitate adjustment of power in the beam of energy based on the angles.

In still another aspect of the present invention, a method of ablating tissue in a patient as a treatment for fibrillation comprises providing an ablation device having an energy source and a sensor. The energy source provides a beam of energy directable to target tissue, and the sensor senses energy reflected back from the target tissue. The ablation device is positioned adjacent the target tissue and a portion of the target tissue is repeatedly scanned. Information about the motion of the target tissue relative to the energy source is calculated. The target tissue is ablated with the beam of energy and the motion is accounted for during the ablation.

The scanning may comprise collecting information about gap distance between the energy source and a surface of the target tissue. The target tissue may comprise tissue in the heart, and the scanning may occur while the heart is beating. Scanning may comprise scanning the target tissue over a short time duration of 5 milliseconds or less. Scanning may comprise repeatedly scanning a single spot.

The calculating may comprise calculating variance, velocity, or acceleration of the target tissue. Accounting for the motion may comprise adjusting the energy beam position or power based on the calculated information. The accounting step may also comprise maintaining gap distance between the energy source and the target tissue within a predetermined range, based on the calculated information. The predetermined range may be from 2 and 20 mm.

The method may further comprise identifying tissue type based on the motion. Sensitive tissue that is unsuitable for ablation may be identified based on the motion. Anatomical structures such as the pulmonary veins may be identified based on the motion. The method may further comprise determining thickness of the target tissue based on the motion.

In yet another aspect of the present invention, a method for of ablating tissue in a patient as a treatment for fibrillation comprises providing an ablation device having an energy source and a sensor. The energy source provides a beam of energy directable to target tissue, and the sensor senses energy reflected back from the target tissue. The ablation device is positioned adjacent the target tissue and a standard lesion ratio from the target tissue is provided. An initial backscatter signal from unablated target tissue is sensed with the sensor and the target tissue is ablated with the beam of energy. A post ablation backscatter signal from the target tissue after ablation is sensed. The current lesion ratio is then compared to the standard lesion ratio, and the ablation is discontinued when the current lesion ratio is greater than or equal to the standard lesion ratio.

The standard lesion ratio may comprise a numerical value associated with a substantially transmural lesion. The standard lesion ratio may comprise a normalized backscatter signal value of a transmural lesion. The standard lesion ratio may also comprise a normalized signal pattern, a frequency, or other unique property of a substantially transmural lesion. Providing the standard lesion ratio may further comprise sensing a tissue backscatter signal in a region of the tissue with high echodensity, sensing a tissue backscatter signal in a region of the tissue with low echodensity, and determining a ratio of the high and the low echodensity backscatter signals. The region of high echodensity may comprise a substantially transmural lesion, and the region of low echodensity may comprise unablated tissue. The standard lesion ratio may comprise a laboratory determined value.

The sensing of the initial backscatter signal may be obtained during a diagnostic sweep of the target tissue prior to ablation thereof, or it may be obtained prior to the ablating, or during the ablating. The ablating may comprise incrementally increasing lesion depth in the ablated tissue. The increments may decrease in value as lesion depth increases or the increments may be of constant value. The ablating may comprise continuously increasing lesion depth in the ablated tissue.

The sensing of the post ablation backscatter signal may occur after each incremental ablation step is performed, or it may occur periodically during the ablation. It may also occur continuously during the ablation. The comparing step may determine if the ablation has created a substantially transmural lesion in the target tissue.

These and other embodiments are described in further detail in the following description related to the appended drawing figures.

BRIEF DESCRIPTION OF THE DRAWINGS

FIGS. 4A-4B illustrate alternative embodiments of an energy source.
FIGS. 5-6 illustrate still other embodiments of an energy source.

DETAILED DESCRIPTION OF THE INVENTION

The following description of the preferred embodiments of the invention is not intended to limit the invention to these preferred embodiments, but rather to enable any person skilled in the art to make and use this invention.

Figure 1:
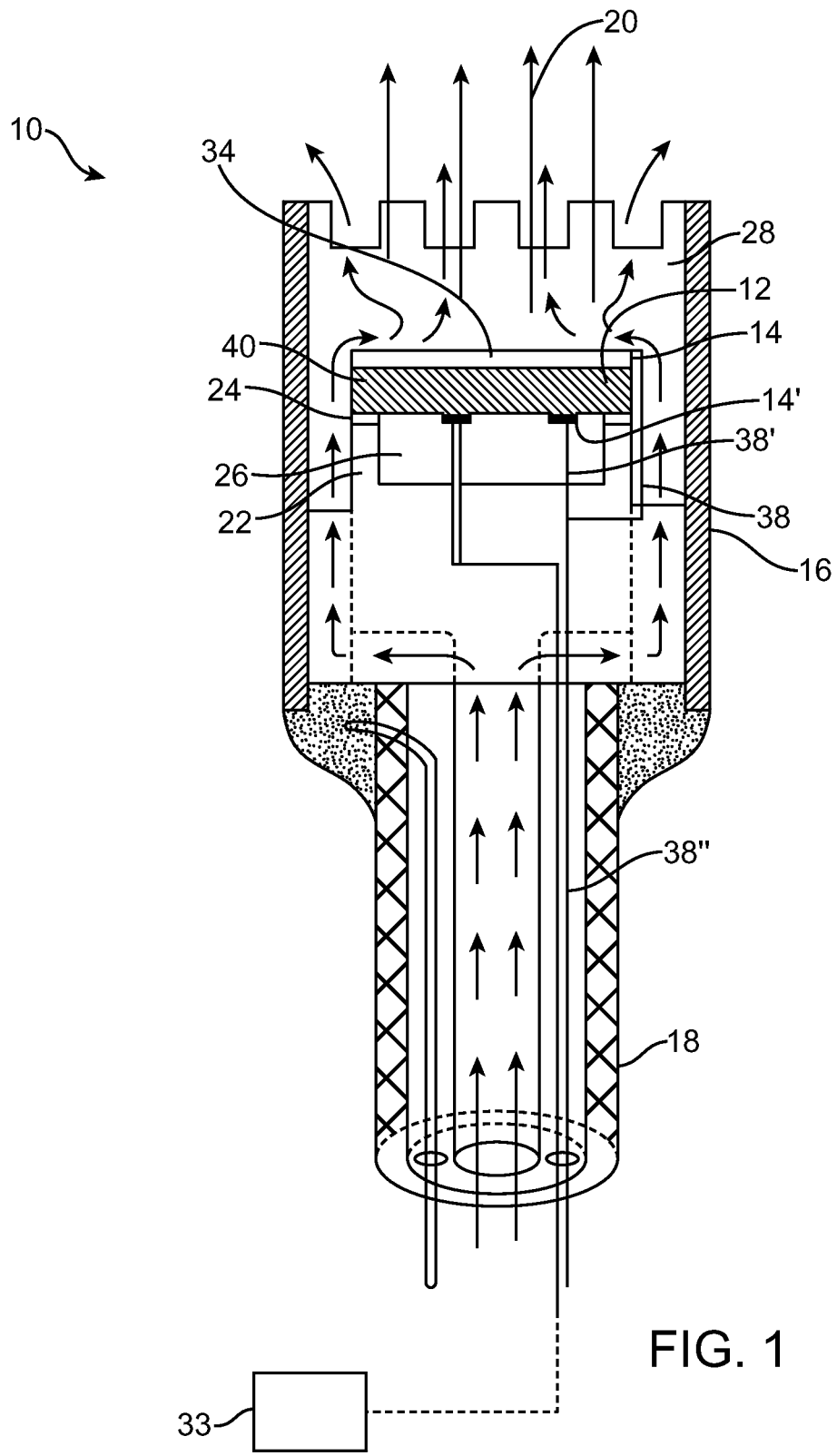
FIG. 1 illustrates an exemplary embodiment of an energy delivery device.

As shown in FIG. 1, the energy delivery system 10 of the preferred embodiments includes an energy source 12, that functions to provide a source of ablation energy, and an electrical attachment 14, coupled to the energy source 12, that functions to energize the energy source 12 such that it emits an energy beam 20. The energy delivery system 10 of the preferred embodiments also includes a sensor 40 or the energy source 12 may also serve as the sensor to detect the gap (distance of the tissue surface from the energy source 12), the thickness of the tissue targeted for ablation, the characteristics of the ablated tissue, and any other suitable parameter or characteristic of the tissue and/or the environment around the energy delivery system 10. The energy delivery system 10 of the preferred embodiments also includes a processor 33 operatively coupled to the sensor and to the electrical attachment 14, that controls the electrical attachment 14 and/or the electrical signal delivered to the energy source 12 based on the information from the sensor 40. The energy delivery system 10 is preferably designed for delivering energy to tissue, more specifically, for delivering ablation energy to tissue, such as heart tissue, to create a conduction block—isolation and/or block of conduction pathways of abnormal electrical activity, which typically originate from the pulmonary veins in the left atrium —for treatment of atrial fibrillation in a patient. The system 10, however, may be alternatively used with any suitable tissue in any suitable environment and for any suitable reason.

The Energy Source. As shown in FIG. 1, the energy source 12 of the preferred embodiments functions to provide a source of ablation energy and emit an energy beam 20. The energy source 12 is preferably moved and positioned within a patient, preferably within the left atrium of the heart of the patient, such that the energy source 12 is positioned at an appropriate angle with respect to the target tissue. The angle is preferably any suitable angle such that the emitted energy beam 20 propagates into the target tissue, and preferably generates a transmural lesion (i.e. a lesion through the thickness of the tissue that preferably creates a conduction block, as described below). Angles between 40 and 140 degrees are preferable because in this range the majority of the energy beam will preferably propagate into the tissue and the lesion depth needed to achieve transmurality is preferably minimally increased from the ideal orthogonal angle.

Figure 2:
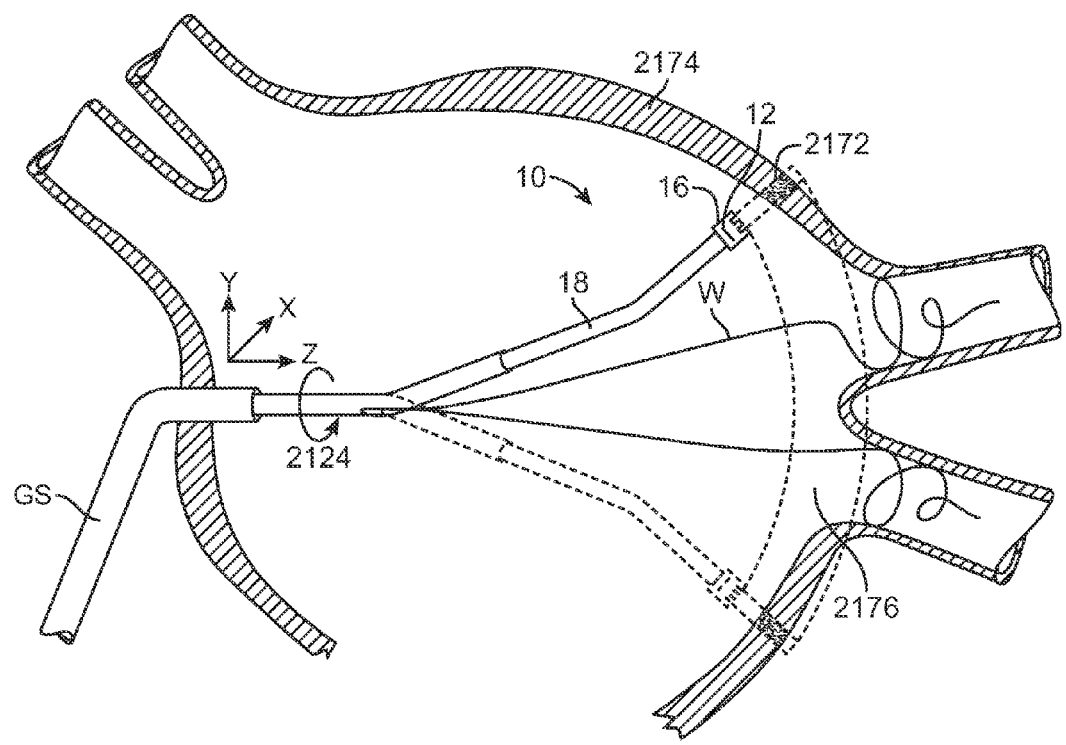
FIG. 2 illustrates exemplary use of the energy delivery device in FIG. 1 to ablate cardiac tissue.

As shown in FIG. 1, the energy source 12 is preferably coupled to a housing 16. The energy source 12 and the housing 16 are preferably positionable within the patient. For example, the housing 16, and the energy source 12 within it, are preferably moved to within the left atrium of the heart (or in any other suitable location) and, once positioned there, are preferably moved to direct the energy source 12 and the emitted energy beam 20 towards the target tissue at an appropriate angle. Furthermore, the housing 16, and the energy source 12 within it, are preferably moved along an ablation path such that the energy source 12 provides a partial or complete zone of ablation along the ablation path. The zone of ablation along the ablation path preferably has any suitable geometry to provide therapy, such as providing a conduction block for treatment of atrial fibrillation in a patient. The zone of ablation along the ablation path may alternatively provide any other suitable therapy for a patient. A linear ablation path is preferably created by moving the housing 16, and the energy source 12 within it, along an X, Y, and/or Z-axis. As shown in FIG. 2, the motion of the distal portion of the elongate member 18 in and out of the guide sheath portion GS of the elongate member 18 is represented by the z-axis. A generally circular or elliptical ablation path is preferably created by rotating the energy source 12 about an axis (for example, as defined by the wires W in FIG. 2). The elongate member 18, along with the housing 16 and the energy source 12, is preferably rotated, as shown in FIG. 2. Alternatively, in other configurations, the energy source 12 is rotated within the housing 16. For example, as shown in FIG. 2, the housing 16 points towards the wall tissue 2174 of an atrium. The energy source 12 in the housing 16 emits an energy beam to establish an ablation window 2172. As the housing 16 (and an elongate member 18, described below) are rotated (as shown by arrow 2124 in FIG. 2), the ablation window 2172 sweeps a generally circular ablation path 2176 creating a section of a conical shell. Further, in this example, it may be desirable to move the elongate member forwards or backwards along the Z-axis to adjust for possible variations in the anatomy. Although the ablation path is preferably linear or circular, any suitable ablation path may be created by any suitable combination of movement in the X, Y, and Z axes and rotational movement.

As shown in FIG. 1, the energy delivery system 10 of the preferred embodiments may also include an elongate member 18, coupled to the energy source 12. The elongate member 18 is preferably a catheter made of a flexible multi-lumen tube, but may alternatively be a cannula, tube or any other suitable elongate structure having one or more lumens. The elongate member 18 of the preferred embodiments functions to accommodate pull wires, fluids, gases, energy delivery structures, electrical wires, therapy catheters, navigation catheters, pacing catheters, connections and/or any other suitable device or element. As shown in FIG. 1, the elongate member 18 preferably includes a housing 16 positioned at a distal portion of the elongate member 18. The elongate member 18 further functions to move and position the energy source 12 and/or the housing 16 within a patient, such that the emitted energy beam 20 propagates into the target tissue at an appropriate angle and the energy source 12 and/or the housing 16 is moved along an ablation path such that the energy source 12 provides a partial or complete zone of ablation along the ablation path.

The energy source 12 is preferably an ultrasound transducer that emits an ultrasound beam, but may alternatively be any suitable energy source that functions to provide a source of ablation energy. Suitable sources of ablation energy include but are not limited to, radio frequency (RF) energy, microwaves, photonic energy, and thermal energy. The therapy could alternatively be achieved using cooled sources (e.g., cryogenic fluid). The energy delivery system 10 preferably includes a single energy source 12, but may alternatively include any suitable number of energy sources 12. The ultrasound transducer is preferably made of a piezoelectric material such as PZT (lead zirconate titanate) or PVDF (polyvinylidine difluoride), or any other suitable ultrasound emitting material. For simplicity, the front face of the transducer is preferably flat, but may alternatively have more complex geometry such as either concave or convex to achieve an effect of a lens or to assist in apodization—selectively decreasing the vibration of a portion or portions of the surface of the transducer—and management of the propagation of the energy beam 20. The transducer preferably has a circular geometry, but may alternatively be elliptical, polygonal, or any other suitable shape. The transducer may further include coating layers which are preferably thin layer(s) of a suitable material. Some suitable transducer coating materials may include graphite, metal-filled graphite, gold, stainless steel, magnesium, nickel-cadmium, silver, and a metal alloy. For example, as shown in FIG. 1, the front face of the energy source 12 is preferably coupled to one or more matching layers 34. The matching layer(s) preferably functions to increase the efficiency of coupling of the energy beam 20 into the surrounding fluid 28. The matching layer 34 is preferably made from a plastic such as parylene, preferably placed on the transducer face by a vapor deposition technique, but may alternatively be any suitable material, such as graphite, metal-filled graphite, metals, or ceramic, added to the transducer in any suitable manner.

Figure 3:
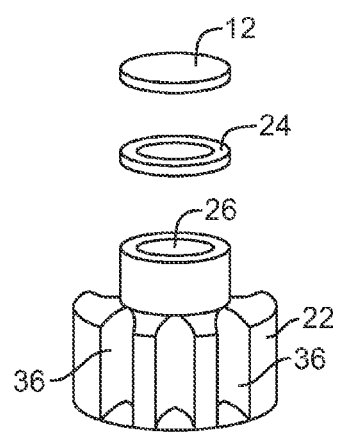
FIG. 3 illustrates an exemplary embodiment of the energy source and backing.

The energy source 12 is preferably one of several variations. In a first variation, as shown in FIG. 3, the energy source 12 is a disc with a flat front surface coupled to a backing 22 with an adhesive ring 24. The backing 22 forms a pocket 26 to help reflect energy in a desired direction, often distally away from the housing 16 into the treatment tissue. A plurality of axial channel or grooves 36 along the backing allow fluid to flow therepast in order to help cool the transducer 12 and prevent direct tissue contact. In a second variation, as shown in FIGS. 4A and 4B, the energy source 12' includes an inactive portion 42. In this variation, the inactive portion 42 does not emit an energy beam when the energy source 12 is energized, or may alternatively emit an energy beam with a very low (substantially zero) energy. The inactive portion 42 preferably functions to aid in the temperature regulation of the energy source, i.e. preventing the energy source from becoming too hot. In a full disk transducer, as shown in FIG. 3, the center portion of the transducer generally becomes the hottest portion of the transducer while energized. By removing the center portion or a portion of the center portion of the transducer, the energy emitted from the transducer is preferably distributed differently across the transducer, and the heat of the transducer is preferably more easily dissipated.

The inactive portion 42 is preferably a hole or gap defined by the energy source 12'. In this variation, a coolant source may be coupled to, or in the case of a coolant fluid, it may flow through the hole or gap defined by the energy source 12' to further cool and regulate the temperature of the energy source 12'. The inactive portion 42 may alternatively be made of a material with different material properties from that of the energy source 12'. For example, the material is preferably a metal, such as copper, which functions to draw or conduct heat away from the energy source 12. Alternatively, the inactive portion is made from the same material as the energy source 12, but with the electrode plating removed or disconnected from the electrical attachments 14 and or the generator. The inactive portion 42 is preferably disposed along the full thickness of the energy source 12', but may alternatively be a layer of material on or within the energy source 12' that has a thickness less than the full thickness of the energy source 12'. As shown in FIG. 4A, the energy source 12' is preferably a doughnut-shaped transducer. As shown, the transducer preferably defines a hole (or inactive portion 42) in the center portion of the transducer. The energy source 12' of this variation preferably has a circular geometry, but may alternatively be elliptical, polygonal as shown in FIG. 4B), or any other suitable shape. The energy source 12' preferably includes a singular, circular inactive portion 42, but may alternatively include any suitable number of inactive portions 42 of any suitable geometry, as shown in FIG. 4B. The total energy emitted from the energy source 12 is related to the surface area of the energy source 12 that is active (i.e. emits energy beam 20). Therefore, the size and location of inactive portion(s) 42 preferably sufficiently reduce the heat build-up in the energy source 12, while allowing the energy source 12 to provide as much output energy as possible or as desired.

In a third variation, as shown in FIG. 5, the energy source 12" preferably includes a plurality of annular transducers 44. The plurality of annular transducers is preferably a plurality concentric rings, but may alternatively have any suitable configuration with any suitable geometry, such as elliptical or polygonal. The energy source 12" may further include an inactive portion 42, such as the center portion of the energy source 12" as shown in FIG. 5. The plurality of annular transducers 44 preferably includes at least a first annular transducer and a second annular transducer. The first annular transducer preferably has material properties that differ from those of the second annular transducer, such that the first annular transducer emits a first energy beam that is different from the second energy beam emitted from the second annular ring. Furthermore, the first annular transducer may be energized with a different frequency, voltage, duty cycle, power, and/or for a different length of time from the second annular transducer. Alternatively the first annular ring may be operated in a different mode from the second annular ring. For example, the first annular ring may be run in a therapy mode, such as ablate mode which delivers a pulse of ultrasound sufficient for heating of the tissue, while the second annular ring may be run in a diagnostic mode, such as A-mode, which delivers a pulse of ultrasound of short duration, which is generally not sufficient for heating of the tissue but functions to detect characteristics of the target tissue and/or environment in and around the energy delivery system. The first annular transducer may further include a separate electrical attachment 14 from that of the second annular transducer.

In a fourth variation, as shown in FIG. 6, the energy source 12''' preferably includes a grid of transducer portions 46. The grid of transducer portions 46 preferably has any suitable geometry such as circular, rectangular (as shown in FIG. 6), elliptical, polygonal, or any other suitable geometry. The energy source 12''' in this variation may further include a transducer portion that is inactive, such as an inactive portion as described in the second variation of the energy source 12'. The grid of transducer portions 46 preferably includes at least a first transducer portion and a second transducer portion. In a first version, the first transducer portion and the second transducer portion are preferably portions of a single transducer with a single set of material properties. The first transducer portion is preferably energized with a different frequency, voltage, duty cycle, power, and/or for a different length of time from the second transducer portion. Furthermore the first transducer portion may be operated in a different mode from the second transducer portion. For example, the first transducer portion may operate in a therapy mode, such as ablate mode, while the second transducer portion may operate in a diagnostic mode, such as A-mode. In this version, the first transducer portion may further include a separate electrical attachment 14 from that of the second transducer portion. For example, the first transducer portion may be located towards the center of the energy source 12''' and the second transducer portion may be located towards the outer portion of the energy source 12''' and the second transducer portion may be energized while the first transducer portion remains inactive. In a second version, the first transducer portion preferably has material properties that differ from those of the second transducer portion, such that the first transducer portion emits a first energy beam that is different from the second energy beam emitted from the second portion. In this version, the first transducer portion may also be energized with a different frequency, voltage, duty cycle, power, and/or for a different length of time from the second transducer portion.

The Electrical Attachment. As shown in FIG. 1, the electrical attachment 14 of the preferred embodiments functions to energize the energy source 12 such that it emits an energy beam 20. In use, as the energy source 12 is energized, it emits an energy beam 20 towards targeted tissue. As the energy is transferred from the energy beam 20 into the tissue, the targeted tissue portion is preferably heated sufficiently to achieve ablation. As shown in FIG. 1, the electrical attachment 14 is preferably coupled to the energy source 12. The energy delivery system 10 preferably includes two electrical attachments 14 and 14', but may alternatively include any suitable number of electrical attachments to energize the energy source 12. The energy source 12 preferably has a first electrical attachment 14 coupled the front surface of the energy source 12 which is coupled to a suitably insulated wire 38. The electrical attachment 14 is preferably accomplished by standard bonding techniques such as soldering, wire bonding, conductive epoxy, or swaging. The electrical attachment 14 is preferably placed closer to the edge of the energy source 12 so as not to disturb the energy beam 20 emitted by the energy source 12 upon being electrically energized. The energy source 12 preferably has a second electrical attachment 14' coupled to the back surface of the energy source 12 which is coupled to a suitably insulated wire 38'. Wires 38 and 38' together form a pair 38", which are preferably a twisted shielded pair, a miniature coaxial cable, a metal tube braid, or are coupled in any other suitable method. The electrical attachment(s) 14 may alternatively be coupled to the energy source 12 in any other suitable fashion in any other suitable configuration.

The energy delivery system 10 of the preferred embodiments also includes an electrical generator (not shown) that functions to provide power to the energy source 12 via the electrical attachment(s) 14. The energy source 12 is preferably coupled to the electrical generator by means of the suitably insulated wires 38 and 38' connected to the electrical attachments 14 and 14' coupled to the two faces of the energy source 12. When energized by the generator the energy source 12 emits energy. The generator provides an appropriate signal to the energy source 12 to create the desired energy beam 20. The frequency is preferably in the range of 5 to 25 MHz, more preferably in the range of 8 to 20 MHz, and even more preferably in the range of 2 to 15 MHz. The energy of the energy beam 20 is determined by the excitation voltage applied to the energy source 12, the duty cycle, and the total time the voltage is applied. The voltage is preferably in the range of 5 to 200 volts peak-to-peak. In addition, a variable duty cycle is preferably used to control the average power delivered to the energy source 12. The duty cycle preferably ranges from 0% to 100%, with a repetition frequency that is preferably faster than the time constant of thermal conduction in the tissue. One such appropriate repetition frequency is approximately 40 kHz.

Figure 7:
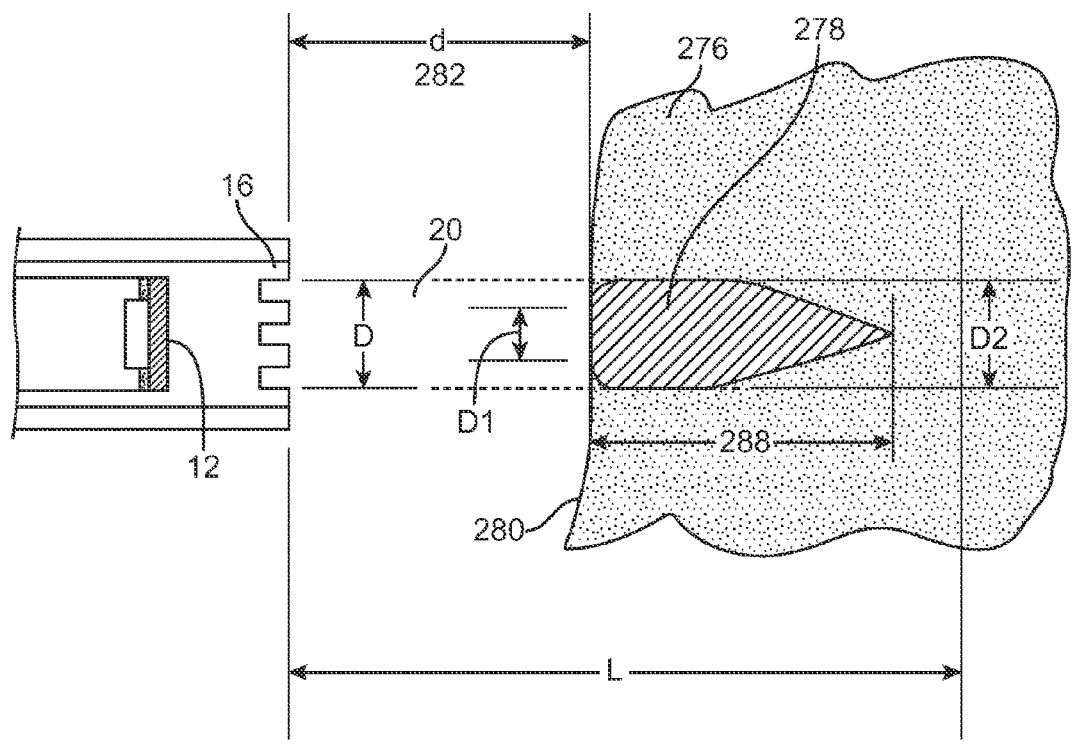
FIG. 7 illustrates the energy beam and zone of ablation in tissue.

Energy Beam and Tissue Interaction. When energized with an electrical signal or pulse train by the electrical attachment 14 and/or 14', the energy source 12 emits an energy beam 20 (such as a sound pressure wave). The properties of the energy beam 20 are determined by the characteristics of the energy source 12, the matching layer 34, the backing 22 (described below), the electrical signal from electrical attachment 14. These elements determine the frequency, bandwidth, and amplitude of the energy beam 20 (such as a sound wave) propagated into the tissue. As shown in FIG. 7, the energy source 12 emits energy beam 20 such that it interacts with tissue 276 and forms a lesion (zone of ablation 278). The energy beam 20 is preferably an ultrasound beam. The tissue 276 is preferably presented to the energy beam 20 within the collimated length L. The front surface 280 of the tissue 276 is at a distance d (282) away from the distal face of the housing 16. As the energy beam 20 travels through the tissue 276, its energy is absorbed and scattered by the tissue 276 and most of the ablation energy is converted to thermal energy. This thermal energy heats the tissue to temperatures higher than the surrounding tissue resulting in a heated zone 278. In the zone 278 where the tissue is heated, the tissue cells are preferably rendered dead due to heat. The temperatures of the tissue are preferably above the temperature where cell death occurs in the heated zone 278 and therefore, the tissue is said to be ablated. Hence, the zone 278 is preferably referenced as the ablation zone or lesion.

The Physical Characteristics of the Lesion. The shape of the lesion or ablation zone 278 formed by the energy beam 20 depends on the characteristics of suitable combination factors such as the energy beam 20, the energy source 12 (including the material, the geometry, the portions of the energy source 12 that are energized and/or not energized, etc.), the matching layer 34, the backing 22 (described below), the electrical signal from electrical attachment 14 (including the frequency, the voltage, the duty cycle, the length and shape of the signal, etc.), and the characteristics of target tissue that the beam 20 propagates into and the length of contact or dwell time. The characteristics of the target tissue include the thermal transfer properties and the ultrasound absorption, attenuation, and backscatter properties of the target tissue and surrounding tissue.

The shape of the lesion or ablation zone 278 formed by the energy beam 20 is preferably one of several variations due to the energy source 12 (including the material, the geometry, the portions of the energy source 12 that are energized and/or not energized, etc.). In a first variation of the ablation zone 278, as shown in FIG. 7, the energy source 12 is a full disk transducer and the ablation zone 278 is a tear-shaped lesion. The diameter D1 of the zone 278 is smaller than the diameter D of the beam 20 at the tissue surface 280 and further, the outer layer(s) of tissue 276 preferably remain substantially undamaged. This is due to the thermal cooling provided by the surrounding fluid (cooling fluid and/or blood), which is flowing past the tissue surface 280. More or less of the outer layers of tissue 276 may be spared or may remain substantially undamaged due to the amount that the tissue surface 280 is cooled and/or the characteristics of the energy delivery system 10 (including the energy source 12 and the energy beam 20). The energy deposited in the ablation zone 278 preferably interacts with the non-surface layer(s) of tissue such that the endocardial surface remains pristine (and/or not charred). As the energy beam 20 travels deeper into the tissue, the thermal cooling is provided by the surrounding tissue, which is not as efficient as that on the surface. The result is that the ablation zone 278 has a larger diameter D2 than D1 as determined by the heat transfer characteristics of the surrounding tissue as well as the continued input of the energy from the beam 20. As the beam 20 is presented to the tissue for an extended period of time, the ablation zone 278 extends into the tissue, but not indefinitely. There is a natural limit of the depth 288 of the ablation zone 278 as determined by the factors such as the attenuation and absorption of the ultrasound energy as the energy beam 20 propagates into the tissue, heat transfer provided by the healthy surrounding tissue, and the divergence of the beam beyond the collimated length L. During this ultrasound-tissue interaction, the ultrasound energy is being absorbed by the tissue, and therefore less and less of it is available to travel further into the tissue. Thus a correspondingly smaller diameter heated zone is developed in the tissue, and the overall result is the formation of the heated ablation zone 278, which is in the shape of an elongated tear limited to a depth 288 into the tissue.

Figure 9:
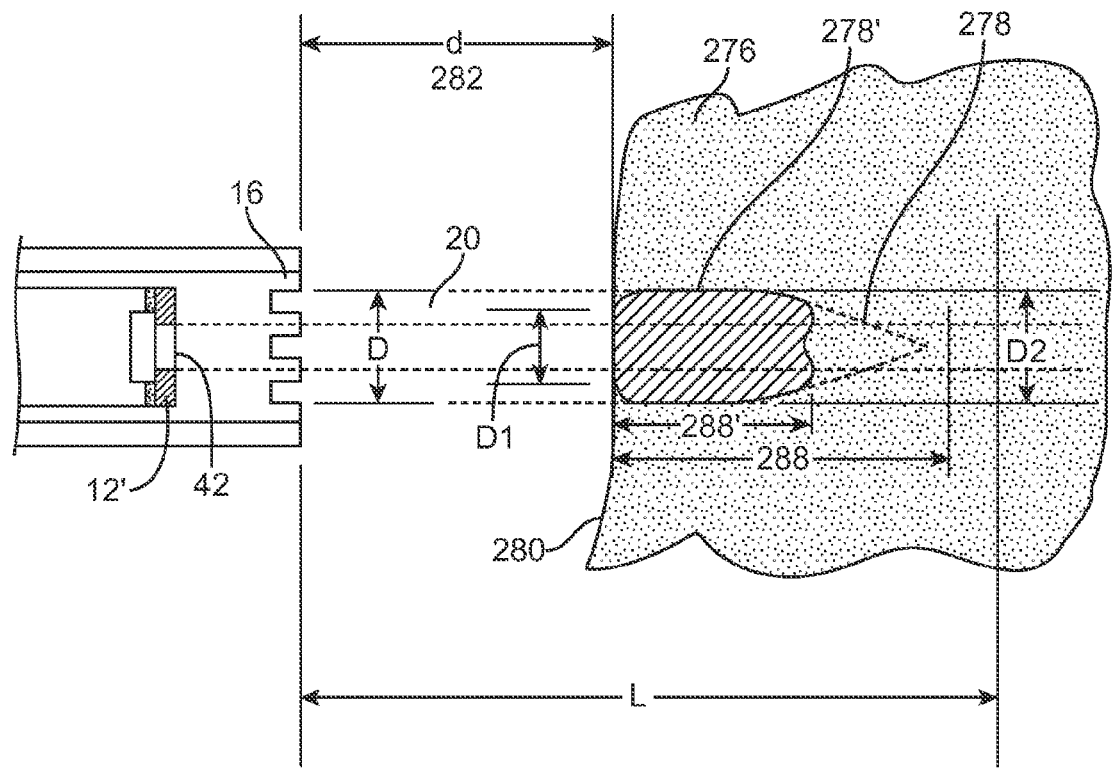
FIGS. 9-10 illustrate the energy beam and zone of ablation in tissue.

In a second variation, as shown in FIG. 9, the ablation zone 278' has a shorter depth 288'. In this variation, the lesion preferably has a more blunt shape than ablation zone 278 (FIG. 7). One possible lesion geometry of this second variation may be a tooth shaped geometry, as shown in FIG. 9, but may alternatively have any suitable shape such as a blunt tear shape, a circular shape, or an elliptical shape. As shown in FIG. 9, zone 278' (similarly to zone 278 in FIG. 7) has a diameter D1 of the zone 278' smaller than the diameter D of the beam 20 at the tissue surface 280 due to the thermal cooling provided by the surrounding fluid flowing past the tissue surface 280. In this variation, the energy source 12' preferably has an inactive portion 42 located at the center of the energy source 12', such that energy source is a doughnut-shaped transducer which emits an energy beam 20 that is generally more diffused, with a broader, flatter profile, than the energy beam 20 of the first variation (FIG. 7). The energy beam 20 emitted from the doughnut-shaped transducer, as shown in FIG. 9, preferably has a reduced peak intensity along the midline of the energy beam (as shown in cross section by the dotted lines in FIG. 9). With this ultrasound-tissue interaction, the reduced peak intensity along the midline of the energy beam is being absorbed by the tissue, and less and less of the energy is available to travel further into the tissue, forming a blunter lesion than in the first variation.

The size and characteristics of the ablation zone also depend on the frequency and voltage applied to the energy source 12 to create the desired energy beam 20. For example, as the frequency increases, the depth of penetration of ultrasound energy into the tissue is reduced resulting in an ablation zone 278 (ref. FIG. 7) of shallower depth 288. The frequency is preferably in the range of 5 to 25 MHz, more preferably in the range from 8 to 20 MHz, and even more preferably in the range from 10 to 18 MHz. The energy of the energy beam 20 is determined by the excitation voltage applied to the energy source 12 for a transducer fabricated from PZT material, for example. The voltage is preferably in the range of 5 to 200 volts peak-to-peak. In addition, a variable duty cycle is preferably used to control the average power delivered to the energy source 12. The duty cycle preferably ranges from 0% to 100%, with a repetition frequency of approximately 40 kHz, which is preferably faster than the time constant of thermal conduction in the tissue. This results in an ablation zone 278, which is created within 1 to 5 seconds, and is of depth 288 of approximately 5 millimeters (mm), and of a maximum diameter of approximately 2.5 mm in correspondence to the diameter of the energy source 12, for an average power level preferably 0.5 to 25 watts, more preferably 2 to 10 watts, and even more preferably 2 to 7 watts.

Figure 8A:
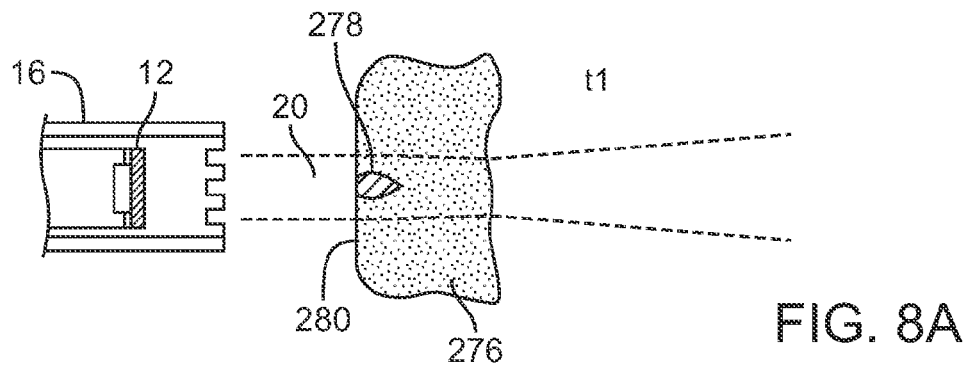
FIGS. 8A-8D illustrate the energy beam and zone of ablation in tissue.
Figure 8B:
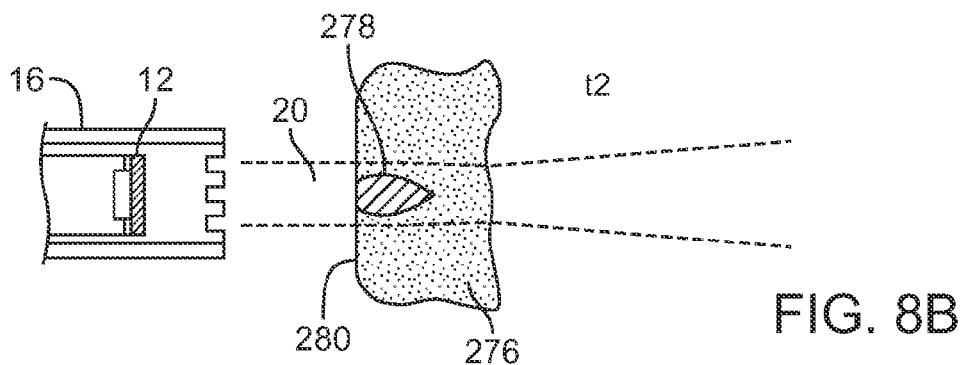
Figure 8C:
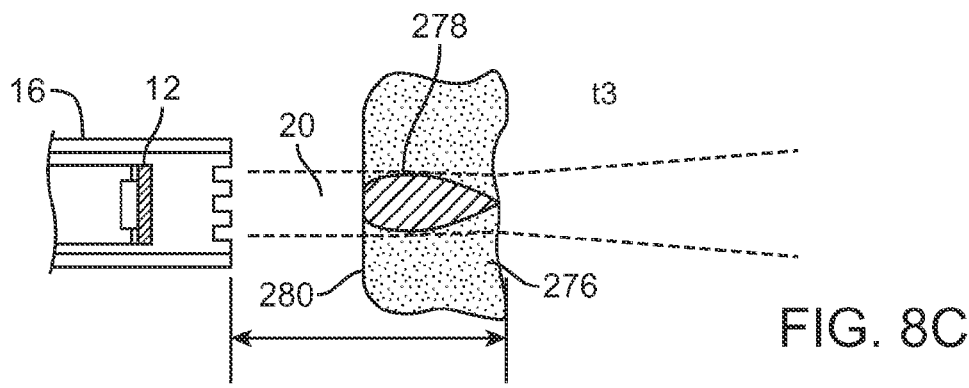
Figure 8D:
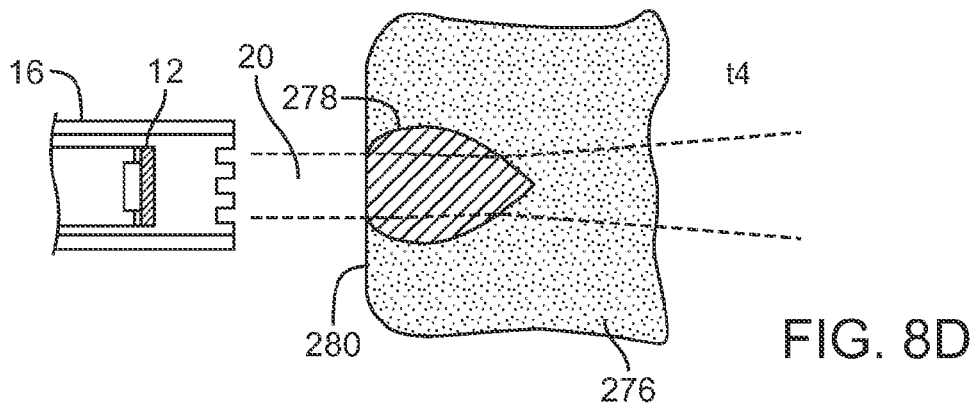

The size and characteristics of the ablation zone 278 also depend on the time the targeted tissue is contacted by the energy beam 20, as shown in FIGS. 8A-8D, which exemplify the formation of the lesion at times $t_1$, $t_2$, $t_3$ and $t_4$, respectively. The ablation zone 278 in the tissue is formed by the conversion of the ultrasound energy to thermal energy in the tissue. As the energy beam 20 initially impinges on the front surface 280 of the tissue 276 at time $t_1$, heat is created which begins to form the lesion 278 (FIG. 8A). As time passes on to $t_2$, and $t_3$ (FIGS. 8B and 8C), the ablation zone 278 continues to grow in diameter and depth. This time sequence from $t_1$ to $t_3$ preferably takes as little as 1 to 5 seconds, depending on the ultrasound energy density. As the incidence of the ultrasound beam is continued beyond time $t_3$, the ablation lesion 278 grows slightly in diameter and length, and then stops growing due to the steady state achieved in the energy transfer from its ultrasound form to the thermal form balanced by the dissipation of the thermal energy into the surrounding tissue. The example shown in FIG. 8D shows the lesion after an exposure t4 of approximately 30 seconds to the energy beam 20. Thus the lesion reaches a natural limit in size and does not grow indefinitely.

The ultrasound energy density preferably determines the speed at which the ablation occurs. The acoustic power delivered by the energy source 12 divided by the cross sectional area of the beam 20 determines the energy density per unit time. Effective acoustic power preferably ranges from 0.5 to 25 watts, more preferably from 2 to 10 watts, and even more preferably from 2 to 7 watts, and the corresponding power densities preferably range from 50 watts/cm$^2$ to 2500 watts/cm$^2$. These power densities are developed in the ablation zone. As the beam diverges beyond the ablation zone, the power density falls such that ablation will not occur, regardless of the time exposure.

Although the shape of the ablation zone 278 is preferably one of several variations, the shape of the ablation zone 278 may be any suitable shape and may be altered in any suitable fashion due to any suitable combination of the energy beam 20, the energy source 12 (including the material, the geometry, etc.), the matching layer 34, the backing 22 (described below), the electrical signal from electrical attachment 14 (including the frequency, the voltage, the duty cycle, the length of the pulse, etc.), and the target tissue the beam 20 propagates into and the length of contact or dwell time.

The Sensor. The energy delivery system 10 of the preferred embodiments also includes a sensor separate from the energy source and/or the energy source 12 may further function as a sensor to detect the gap (the distance of the tissue surface from the energy source 12), the thickness of the tissue targeted for ablation, the characteristics of the ablated tissue, the incident beam angle, and any other suitable parameter or characteristic of the tissue and/or the environment around the energy delivery system 10, such as the temperature. By detecting the information, the sensor (coupled to the processor, as described below) preferably functions to guide the therapy provided by the ablation of the tissue.

The sensor is preferably one of several variations. In a first variation, the sensor is preferably an ultrasound transducer that functions to detect information with respect to the gap, the thickness of the tissue targeted for ablation, the characteristics of the ablated tissue, and any other suitable parameter or characteristic. The sensor preferably has a substantially identical geometry as the energy source 12 to insure that the area diagnosed by the sensor is substantially identical to the area to be treated by the energy source 12. More preferably, the sensor is the same transducer as the transducer of the energy source, wherein the energy source 12 further functions to detect information by operating in a different mode (such as A-mode, defined below).

Figure 10:
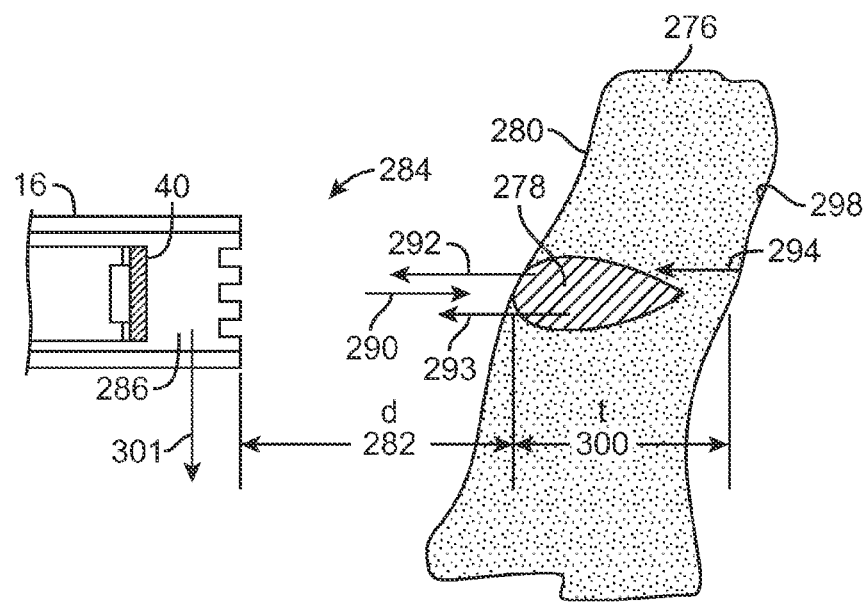

The sensor of the first variation preferably utilizes a burst of ultrasound of short duration, which is generally not sufficient for heating of the tissue. This is a simple ultrasound imaging technique, referred to in the art as A Mode, or Amplitude Mode imaging. As shown in FIG. 10, sensor 40 preferably sends a burst 290 of ultrasound towards the tissue 276. A portion of the beam is reflected and/or backscattered as 292 from the front surface 280 of the tissue 276. This returning sound wave 292 is detected by the sensor 40 a short time later and converted to an electrical signal, which is sent to the electrical receiver (not shown). The returning sound wave 292 is delayed by the amount of time it takes for the sound to travel from the sensor 40 to the front boundary 280 of the tissue 276 and back to the sensor 40. This travel time represents a delay in receiving the electrical signal from the sensor 40. Based on the speed of sound in the intervening media (fluid 286 and blood 284), information regarding the gap distance d (282) is detected. As the sound beam travels further into the tissue 276, a portion 293 of it is scattered from the lesion 278 being formed and travels towards the sensor 40. Again, the sensor 40 converts this sound energy into electrical signals and a processor (described below) converts this information into characteristics of the lesion formation such as thickness, etc. As the sound beam travels still further into the tissue 276, a portion 294 of it is reflected from the back surface 298 and travels towards the transducer. Again, the sensor 40 converts this sound energy into electrical signals and the processor converts this information into the thickness t (300) of the tissue 276 at the point of the incidence of the ultrasound burst 290. As the catheter housing 16 is traversed in a manner 301 across the tissue 276, the sensor 40 detects the gap distance d (282), lesion characteristics, and the tissue thickness t (300). The sensor preferably detects these parameters continuously, but may alternatively detect them periodically or in any other suitable fashion. This information is used to manage the delivery of continuous ablation of the tissue 276 during therapy as discussed below.

In a second variation, the sensor is a temperature sensor that functions to detect the temperature of the target tissue, the surrounding environment, the energy source 12, the coolant fluid as described below, and/or the temperature of any other suitable element or area. The temperature senor is preferably a thermocouple, but may alternatively be any suitable temperature sensor, such as a thermistor or an infrared temperature sensor. This temperature information gathered by the sensor is preferably used to manage the delivery of continuous ablation of the tissue 276 during therapy and to manage the temperature of the target tissue and/or the energy delivery system 10 as discussed below.

The Processor. The energy delivery system 10 of the preferred embodiments also includes a processor 33 (illustrated in FIG. 1), coupled to the sensor 40 and to the electrical attachment 14, that controls the electrical attachment 14 and/or the electrical signal delivered to the electrical attachment 14 based on the information from the sensor 40. The processor 33 is preferably a conventional processor, but may alternatively be any suitable device to perform the desired functions.

The processor 33 preferably receives information from the sensor such as information related to the gap distance, the thickness of the tissue targeted for ablation, the characteristics of the ablated tissue, and any other suitable parameter or characteristic. Based on this information, the processor preferably controls the energy beam 20 emitted from the energy source 12 by modifying the electrical signal sent to the energy source 12 via the electrical attachment 14 such as the frequency, the voltage, the duty cycle, the length of the pulse, and/or any other suitable parameter. The processor preferably also controls the energy beam 20 by controlling portions of the energy source 12 that are energized using various frequencies, voltages, duty cycles, etc. Different portions of the energy source 12 may be energized as described above with respect to the plurality of annular transducers 44 and the grid of transducer portions 46 of the energy source 12" and 12''' respectively. Additionally, the processor may further be coupled to a fluid flow controller. The processor preferably controls the fluid flow controller to increase or decrease fluid flow based on the sensor detecting characteristics of the ablated tissue, of the unablated or target tissue, the temperature of the tissue and/or energy source, and/ or the characteristics of any other suitable condition.

By controlling the energy beam 20 (and/or the cooling of the targeted tissue or energy source 12), the shape of the ablation zone 278 is controlled. For example, the depth 288 of the ablation zone is preferably controlled such that a transmural lesion (a lesion through the thickness of the tissue) is achieved. Additionally, the processor preferably functions to minimize the possibility of creating a lesion beyond the targeted tissue, for example, beyond the outer atrial wall. If the sensor detects the lesion and/or the ablation window 2172 (as shown in FIG. 2) extending beyond the outer wall of the atrium or that the depth of the lesion has reached or exceeded a preset depth, the processor preferably turns off the generator and/or ceases to send electrical signals to the electrical attachment(s) 14.

Additionally, the processor preferably functions to maintain a preferred gap distance between the energy source and the tissue to be treated. The gap distance is preferably between 2-25 mm, more preferably between 2-20 mm, and even more preferably between 2-15 mm. If the sensor detects the lesion and/or the ablation window 2172 (as shown in FIG. 2) extending beyond the outer wall of the atrium or if it does not reach the outer wall of the atrium, or that the depth of the lesion has either not reached or has exceeded a preset depth, the processor preferably repositions the energy delivery system. For example, as the housing 16 (and an elongate member 18, described below) are rotated (as shown by arrow 2124 in FIG. 2), the ablation window 2172 preferably sweeps a generally circular ablation path 2176 creating a section of a conical shell. However, if the sensor determines that the ablation window 2172 is not reaching the wall of the atrium, the processor preferably moves the elongate member forwards or backwards along the Z-axis, or indicates that it should be moved, to adjust for the possible variations in the anatomy. In this example, the operator can reposition the elongate member, or the processor is preferably coupled to a motor drive unit or other control unit that functions to position the elongate member 18.

Figure 11:
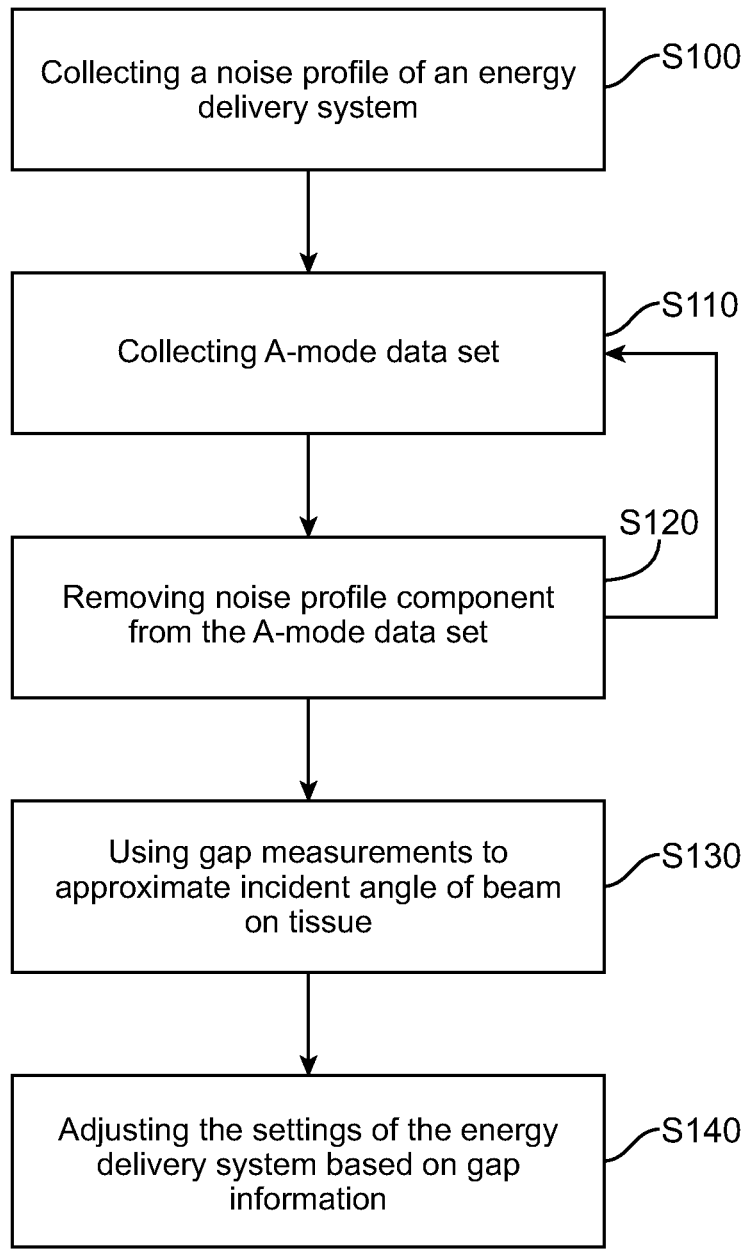
FIG. 11 illustrates a flowchart of an exemplary method for collecting gap data.

Gap Data Collection Method. As shown in FIG. 11, a preferred method to collect noise-reduced gap data in an energy delivery system includes collecting a noise profile of an energy delivery system S100, collecting an A-mode data set S110, and removing noise profile component from the A-mode data set S120. The noise-reduced gap data method preferably functions to measure the gap distance (the distance between the tissue surface and the energy source) with a reduced signal to noise ratio. The collection of noise-reduced gap data preferably occur continuously or periodically during the ablation of tissue, but the noise-reduced gap data may alternatively be collected during a diagnostic sweep of the tissue prior to an ablation sweep or at any other suitable time.

Step S100, which recites collecting a noise profile of an energy delivery system, functions to collect a set of data that represents the noise signal received during normal measurements. The noise profile is preferably an average amplitude value from a set of samples obtained in an echo-less environment (not during normal operation conditions). The noise profile may also be a signal pattern, a frequency band, a set of signals, or any other parameter that may be recognized as the noise component. During A-mode sampling, the echo component is the desired signal. Thus, by measuring the noise profile, the processor can isolate the echo component (the portion of the signal that has been reflected off a tissue surface) from the data. The noise profile may be a signal composed of electrical noise, backscatter noise of a fluid, sensor/component noise, or any other type of noise or combination of noise signals that are not a part of the echo component.

The step of collecting a noise profile is preferably performed by positioning the energy delivery system 10 in a dish of saline solution and collecting samples. The energy delivery system 10 may alternatively be positioned or held in any suitable solution or material to create or simulate an echoless environment. More preferably, Step S100 is performed during a calibration mode and it includes storing the data as a noise profile. The calibration mode is preferably activated by the user or alternatively may be automatically run prior to operation or activated in any suitable manner. Alternatively, the processor may average a large number of A-mode lines while the energy delivery system 10 is deployed. In this alternative, any return signals from a real target is randomly located and over time would preferably average out to a baseline noise profile. The A-mode lines used for the averaged noise profile may be from a set number of samples during the lifetime use of the energy delivery system, or may alternatively be from an initial calibration sweep performed at the beginning of a procedure.

Step S110, which recites collecting an A-mode data set, functions to collect the normal diagnostic data. Step S110 is preferably repeated continuously or periodically during an ablation process. Step S110 is preferably performed in a manner identical to that described above with respect to the sensor.

Step S120, which recites removing the noise profile component from the A-mode data set, functions to isolate the gap distance signal from the noise. Preferably, the average value of the noise profile is subtracted from the A-mode data set. The result is preferably a signal dependent on the gap distance. Alternatively, if the noise profile component is contained within a certain frequency bandwidth, the processor preferably filters (with, for example, a lowpass, highpass, bandpass, or bandstop filter) the signal to isolate the gap distance signal. Any other suitable signal processing method may be used to isolate the gap distance signal.

Steps S110 and S120 are preferably repeated continuously or periodically during the ablation of tissue. Repeating Steps S110 and S120 functions to collect the gap data during the ablation process so the gap distance may be known at the time of the ablation process. The gap data may alternatively be collected during a diagnostic sweep of the tissue prior to the ablation sweep.

The preferred method to collect noise-reduced gap data may also include using multiple gap distances to approximate incident angle of beam on tissue S130. Step S130 is preferably performed after Step S120. The processor preferably stores gap data taken continuously or periodically during the ablation process or alternatively information stored during a diagnostic sweep prior to the ablation sweep. Preferably, three consecutive or closely spaced gap distances are used to calculate the angle of incidence of the energy delivery system. Alternatively, any suitable number of points may be used. The angle of incidence may be used in further steps to improve the interaction of the ultrasound energy beam with the tissue during the ablation process and, ultimately, create a desired transmural lesion of the tissue.

The preferred method to collect noise-reduced gap data may also include adjusting the settings of the energy delivery system based on gap data S140. Step S140 is preferably performed after Step S130. Step S140 functions to adjust the ablation process to account for fluctuations in gap distance and/or angle and may function to prevent damage to the tissue or the device. Based on the gap distance and/or beam incidence angle, the processor preferably controls the energy beam emitted from the energy source by modifying the electrical signal sent to the energy source via the electrical attachment such as the frequency, the voltage, the duty cycle, the length of the pulse, dwell time, and/or any other suitable parameter. The processor may alternatively reposition the energy delivery device.

Figure 12:
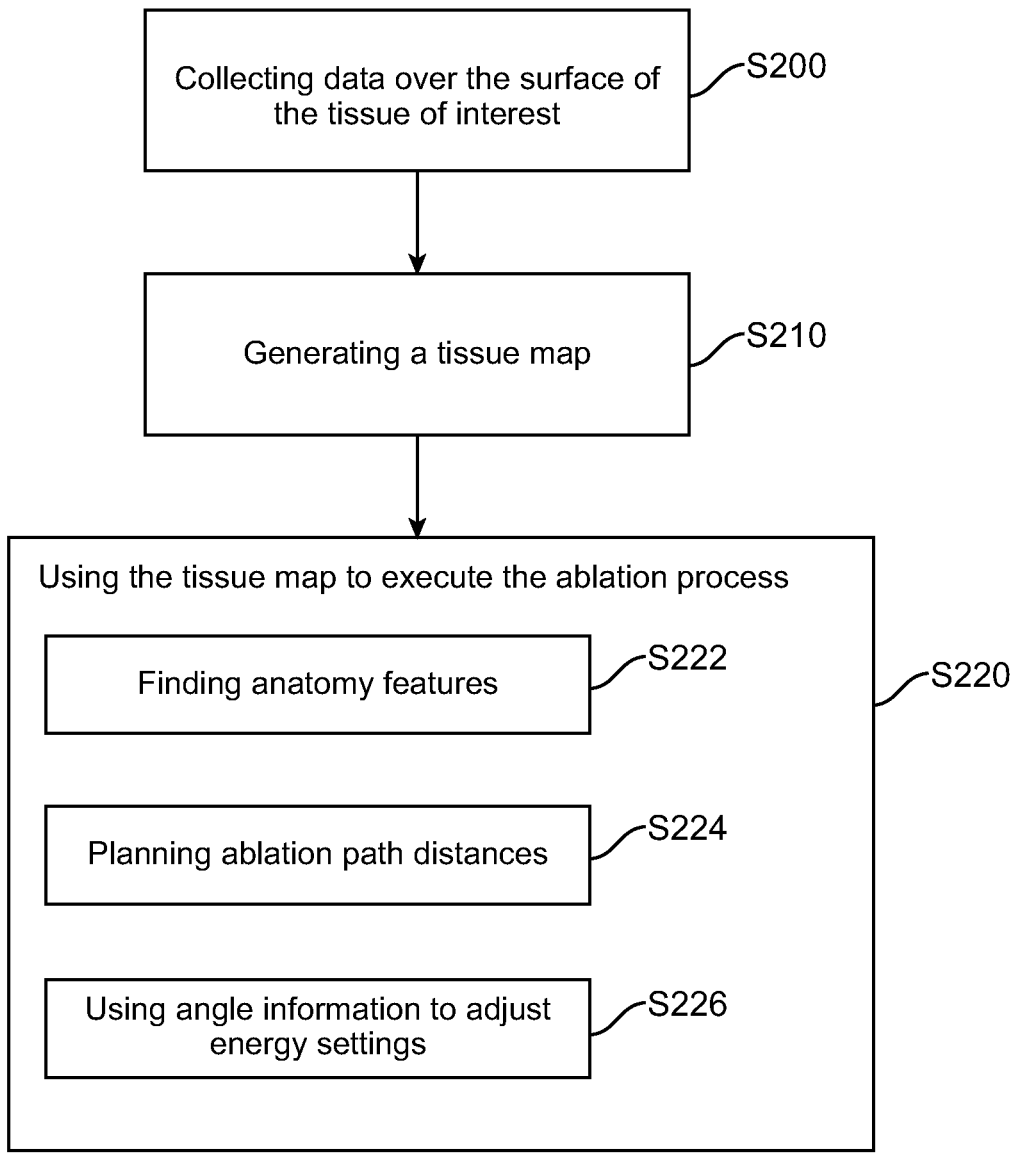
FIG. 12 illustrates a flowchart of an exemplary method for pre-mapping tissue.

Pre-mapping method. As shown in FIG. 12, a preferred method of pre-mapping includes collecting data over the surface of the tissue of interest S200, generating a tissue map S210, and using the tissue map to execute the ablation process S220. The pre-mapping method, which is preferably performed as part of a diagnostic sweep prior to the ablation process, functions to create an anatomical map of the tissue to be used during the ablation process. The pre-mapping method may further function to identify anatomical elements such as the pulmonary vein.

Step S200, which recites collecting data of the surface of the tissue of interest, functions to move the energy delivery system systematically over the tissue, periodically collecting gap distance data. The energy delivery system is preferably moved over the tissue in a horizontal zig-zag pattern, but the energy delivery system may alternatively be moved over the surface in any suitable pattern that sufficiently captures data for the tissue of interest. The path is preferably a singular continuous path but may alternatively include multiple discontinuous paths to capture tissue features from varying angles. As the energy delivery system moves above the surface of the tissue, the sensor preferably collects gap data using a method similar to that described above.

Step S210, which recites generating a tissue map, functions to generate a computer model of the tissue surface. The computer model is preferably generated using the gap data collected during Step S200 by associating the gap distance with the position of the energy delivery system during the data collection. The model preferably provides relative distance information for the surface. The model may additionally and/or alternatively may be used to interpolate the surface angles and contours. The computer model is preferably represented as a 2D image (to take advantage of image processing techniques), a 3D point cloud, 3D surface, or any other suitable format.

Step S220, which recites using the tissue map to execute the ablation process, functions to predict ablation paths and energy delivery system settings. Step S220 preferably includes the sub-steps finding anatomy features S222, planning ablation path distances S224, and using angle information to adjust energy settings S226.

SubStep S222, which recites finding anatomy features, functions to identify anatomical structures to obtain the orientation of the energy delivery system within the heart cavity. Preferably, the pulmonary vein is identified as an area that defines a recess in the surface of the model. Alternatively, other anatomical features may be identified by size, shape, or any other suitable characteristic from the tissue map.

SubStep S224, which recites planning ablation path distances, functions to create a route with optimized gap distances that the energy delivery system will move through. The ablation path preferably has circular geometry, but may alternatively be elliptical, polygonal, or any other suitable shape. The gap distances from the tissue for each position are set to an optimal distance for the ablation process, preferably between 2-25 mm, more preferably between 2-20 mm, and even more preferably between 2-15 mm.

SubStep 226, which recites using angle information to adjust energy settings, functions to optimize the beam energy for proper transmural lesions. The processor preferably makes appropriate changes to the frequency, voltage, duty cycle, power, and/or dwell time of the energy delivery system.

Figure 13:
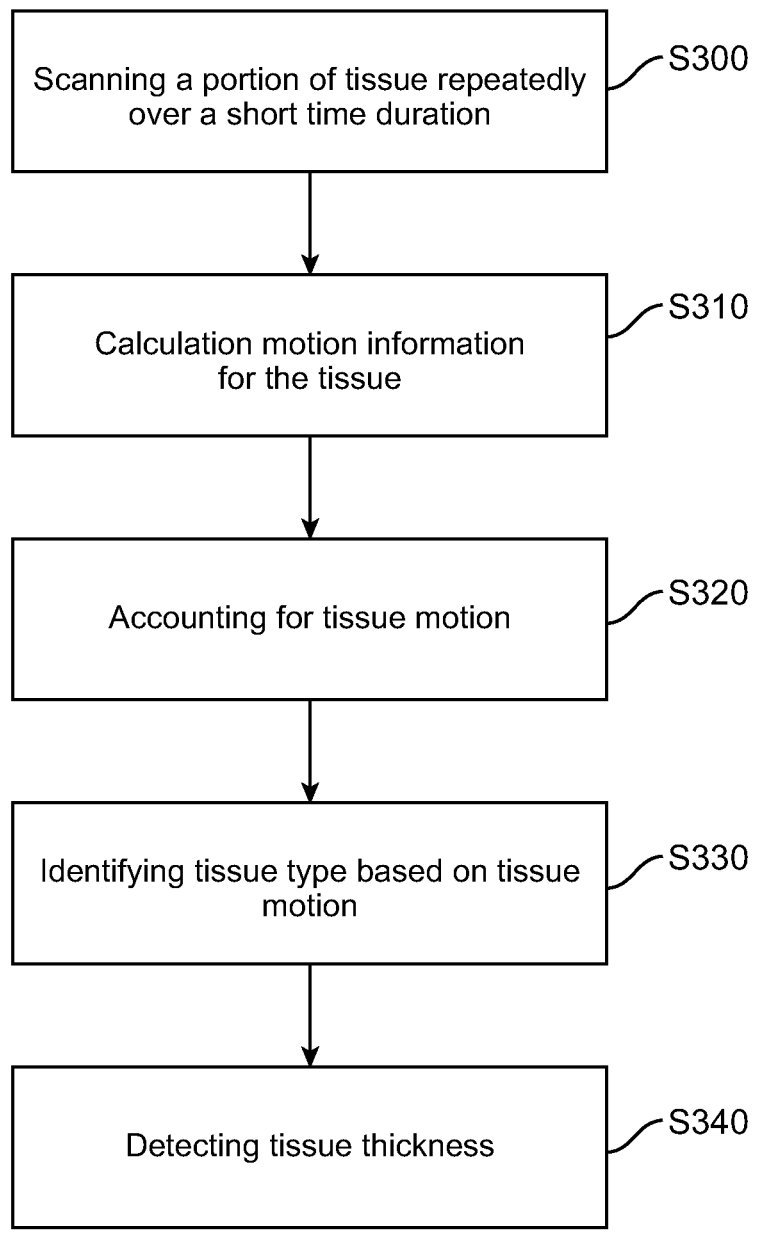
FIG. 13 illustrates a flowchart of an exemplary method for accommodating tissue motion.

Method for Detecting Wall Motion. As shown in FIG. 13, the preferred method for detecting wall motion includes scanning a portion of tissue repeatedly over a short time duration S300, calculating the motion information for the tissue S310, and accounting for tissue motion S320. The preferred method provides information to more accurately determine if and when the device has achieved transmurality, which may reduce the potential damage of the tissue, insufficient ablation of the tissue, or damage to the device.

Step S300, which recites scanning a portion of tissue repeatedly over a short time duration, functions to collect sample gap data (the data set of the separation between the tissue and the energy delivery system) during the periodic motion of the heart tissue. Preferably, the sensor interrogates a singular spot of the tissue (or a group of closely spaced points) multiple times during a brief period of time (preferably over the time span of 5 ms or less, based on the necessary Nyquist sampling frequency for a heart rate of 100 beats per minute. The gap data obtained during the interrogation for a static system will generally remain constant, but—in the case of moving tissue—the gap data will generally vary over time. Alternatively, the gap data may be collected during a normal (preferably slow moving) diagnostic scan, where a singular spot is not repeatedly interrogated. In this alternative, closely spaced points are approximated as a single point, and the motion is approximated over the area defined by these points.

Step S310, which recites calculating motion information for the tissue, functions to generate the variance, velocity, and/or acceleration values for the tissue to be used in Step S320. The processor preferably calculates the variance of an A-mode data set, but the processor may calculate the variance on any suitable data. The variance preferably corresponds to the amplitude of the periodic displacement of the tissue. The motion variance is preferably used to position the energy delivery system 10, and set the parameters of the energy beam used for ablation.

Step S320, which recites accounting for tissue motion, functions to alter the position or energy beam settings of the energy delivery system. Step S320 may further function to ensure that a transmural tissue lesion is created during ablation. Preferably, the processor uses the variance of motion calculated in Step S310. The variance is preferably used to position the energy delivery system such that the gap distance is maintained within a suitable gap distance range. The gap distance is preferably maintained preferably between 2 and 25 mm, more preferably between 2 and 20 mm, and even more preferably between 2 and 15 mm. Alternatively, the energy beam may be set to accommodate for the variance in position.

In an alternative embodiment, Steps S310 and S320 may use the velocity and/or acceleration to predict motion. In this alternative, Step S310 preferably includes the calculation of velocity, acceleration, frequency, and/or any other property of the tissue motion. The processor preferably uses the calculated motion parameters and the periodic motion of the heart to predict the gap distance at any given time. In Step 320, knowledge of the exact gap distance is then used to reposition and change the energy beam settings for near optimal tissue ablation.

As an additional step, the method may include identifying tissue type based on tissue motion S330. This step functions to identify sensitive tissue (tissue not to be ablated) or anatomical structures to use as a referential positioning. The processor preferably compares the recorded motion of the tissue to an anatomical model of tissue. The model may be an average variance of motion or may be more fully defined including modeling of surrounding tissue. The tissue velocity, magnitude of motion, motion frequency, or any other suitable characteristic obtained from the motion profile can be used to distinguish different types of tissue. As an example of tissue identification, the atrial wall tends to move much more than the connective tissues around the heart. The processor may distinguish the two types of tissue by the magnitude of motion variance.

As an additional step, the method may further include detecting tissue thickness S340. Step S340 functions to prevent over and under ablation of tissue. The variance of tissue motion corresponds indirectly with tissue thickness (greater variance corresponds to thinner tissue and, in contrast, small variance corresponds to greater thickness). Preferably, the tissue thickness is based on the variance of tissue motion. Alternatively, the mechanical properties of average tissue such as stiffness are known and kinematic models of the tissue can be used for comparison and identification of tissue.

Figure 14:
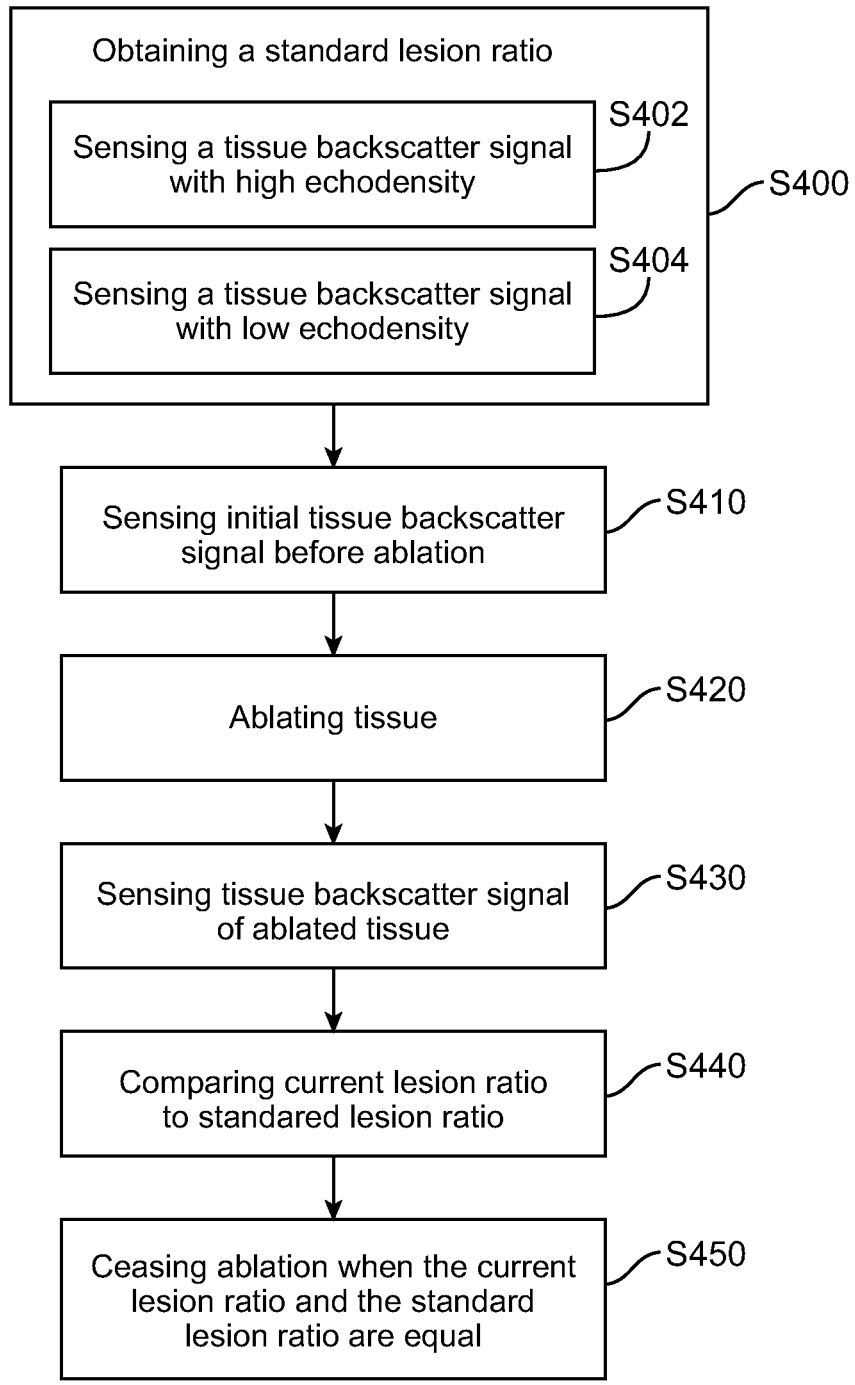
FIG. 14 illustrates a flowchart of an exemplary method for monitoring lesion depth during ablation.

Method of Monitoring Lesion Depth. As shown in FIG. 14, the method of monitoring lesion depth during ablation includes obtaining a standard lesion ratio S400, sensing initial tissue backscatter signal before ablation S410, ablating tissue S420, sensing tissue backscatter signal of ablated tissue S430, comparing current lesion ratio to standard lesion ratio S440, and ceasing ablation when the current lesion ratio and the standard lesion ratio are equal S450. Monitoring the lesion depth during ablation functions to form a desired transmural lesion and prevents over-ablation of the tissue.

Step S400, which recites obtaining a standard lesion ratio, functions to generate a numerical value (the standard lesion ratio) that is associated with a transmural lesion. The standard lesion ratio further functions as a value to which other lesion ratios can be compared to assess if transmurality has been reached. Preferably, the standard lesion ratio is a normalized backscatter signal value of a transmural lesion. Alternatively, the standard lesion ratio may be a normalized signal pattern, a frequency, or any other signal property that is unique for a transmural lesion. Step S400 is preferably performed with two sub-steps including sensing a tissue backscatter signal with high echodensity S402, and sensing a tissue backscatter signal with low echodensity S404. The ratio of the tissue backscatter signal with high echodensity and the tissue backscatter signal with low echodensity preferably make up the standard lesion ratio. Alternatively, the standard lesion ratio may be a laboratory-determined value, which is preprogrammed into the processor, or any other suitable value.

Step S402, which recites sensing a tissue backscatter signal with high echodensity, functions to obtain a signal sample of tissue where a transmural lesion is present. Preferably, the sensor detects an ultrasound reflection from tissue with a transmural lesion. More preferably, the lesion results in increased backscatter and an attenuation of ultrasound. The amount of backscatter and attenuation preferably distinguish the tissue backscatter signal of ablated tissue from tissue that has not undergone ablation.

Step S404, which recites sensing a tissue backscatter signal with low echodensity, functions to obtain a signal sample of tissue that has not undergone ablation. Preferably, the sensor detects an ultrasound reflection from tissue that has not undergone ablation, but is of similar thickness to the high echodensity sample. Tissue of similar thickness may be obtained by scanning tissue with close proximity to that of the ablated tissue sample, tissue with similar wall motion, or identical location (but measuring the low echodensity signal before ablation occurs) or any other suitable combination of locations with similar tissue thicknesses. Alternatively, the sensor may detect an ultrasound reflection from a portion of tissue that was occluded (in a shadow) during ablation. In most situations, the tissue without a lesion has less backscatter and less attenuation of ultrasound than tissue with a lesion.

Step S410, which recites sensing initial tissue backscatter signal before ablation, functions to obtain the tissue backscatter signal with low echodensity for the current lesion ratio. Preferably, the signal is sensed right before ablation begins for a portion of tissue. Alternatively, the initial tissue backscatter signal may be obtained for all points during a diagnostic sweep of the tissue. As another alternative, the initial tissue backscatter signal may be sampled repeatedly during the ablation by sensing the tissue backscatter signal from tissue of close proximity, tissue occluded during ablation (in the beam shadow), or any other suitable location.

Step S420, which recites ablating tissue, functions to increase the lesion depth of the tissue by ablating the tissue in an incremental amount. Step S420 is preferably repeated several times during the course of the method. In a first variation, the ablation steps (i.e., the depth of ablation during one cycle of Step S410) incrementally add to approach transmurality of the tissue, moving from gross ablation steps to small ablation steps. During the first iteration of Step S420, the ablation of the tissue is such that transmurality is not expected, but the ablation step is large enough to ablate a significant portion of the tissue without over ablating the tissue. In further iterations, the ablation preferably approaches the state of transmurality in an approximately asymptotic manner; each step is a smaller ablation depth. The final iteration preferably achieves transmurality. Additionally, estimation of tissue thickness made by the sensor or from an outside source may be used to more efficiently determine ablation steps. In a second variation, each ablation step may be identical in size regardless of iteration or thickness estimation. As another alternative, ablation may occur continuously if Step S430 and Step S440 also occur continuously or periodically during the process.

Step S430, which recites sensing tissue backscatter signal of ablated tissue, functions to obtain the tissue backscatter signal with high echodensity for the current lesion ratio. The sensing of the tissue backscatter signal preferably occurs after each ablation step is completed and preferably occurs periodically or continuously. The sensing of the tissue backscatter signal may, however, occur at any other appropriate time.

Step S440, which recites comparing current lesion ratio to standard lesion ratio, functions to assess if transmurality has been reached. Preferably, the current lesion ratio is based on the initial tissue backscatter signal obtained in Step S410 and the tissue backscatter signal during ablation of Step S430. The current lesion ratio is then compared to the standard lesion ratio obtained in Step S400. If the current lesion ratio is less than the standard lesion ratio (i.e., transmurality has not been reached), ablation preferably continues and Steps S420, S430, and S440 are preferably repeated. If the values are equal (i.e., transmurality has been reached or exceeded), the process proceeds to Step S450. Alternatively, any suitable means of comparing the ratios may be used, including comparisons that do not rely upon actual ratios but rather other numerical values.

Step S450, which recites ceasing ablation when the current lesion ratio and the standard lesion ratio are equal (or within a predetermined threshold of equity), functions to end the ablation process for the tissue. After Step 450, the energy delivery system preferably moves to the next section of tissue to be ablated.

As a person skilled in the art will recognize from the previous detailed description and from the figures and claims, modifications and changes can be made to the preferred embodiments of the invention without departing from the scope of this invention defined in the following claims.

What is claimed is:

1. A method of ablating tissue in a patient as a treatment for fibrillation, said method comprising:
    providing an ablation device having only a single ultrasound transducer;
    positioning the ablation device adjacent a target tissue;
    moving the ablation device over a surface of the target tissue;
    delivering a collimated beam of ultrasound energy to the target tissue with the single ultrasound transducer;
    sensing energy reflected back from the target tissue with the single ultrasound transducer;
    measuring a gap distance between the single ultrasound transducer and the surface of the target tissue, based on the sensed energy reflected back from the target tissue, while the ablation device moves over the surface of the target tissue, thereby generating a plurality of gap distances;
    mapping the plurality of gap distances measured over the surface of the target tissue, thereby generating a map of the target tissue;
    ablating the target tissue with the collimated beam of ultrasound energy;
    maintaining a gap between the single ultrasound transducer and the target tissue so that there is no contact between the single ultrasound transducer and the target tissue while moving the ablation device, delivering the beam of energy, and sensing the energy reflected back from the target tissue; and
    using the tissue map to plan one or more ablation paths and adjust energy delivery settings.

2. The method of claim 1, wherein the positioning of the ablation device comprises advancing the ablation device into a left atrium of the heart.

3. The method of claim 1, wherein moving the ablation device comprises moving the ablation device in a zig-zag pattern.

4. The method of claim 1, wherein moving the ablation device comprises moving the ablation device in a continuous path.

5. The method of claim 1, wherein the map is generated as part of a diagnostic sweep of the target tissue prior to the ablating step.

6. The method of claim 1, wherein the map comprise identification of anatomical structures in the target tissue.

7. The method of claim 6, wherein the anatomical structures comprise the pulmonary veins.

8. The method of claim 1, wherein the map indicates surface contours and angles of the target tissue.

9. The method of claim 1, wherein the map comprises a two dimensional representation of the target tissue.

10. The method of claim 1, wherein the map comprises a three dimensional representation of the target tissue.

11. The method of claim 1, wherein the ablating step creates a continuous lesion in the target tissue, the lesion blocking aberrant electrical pathways in the tissue so as to reduce or eliminate the fibrillation.

12. The method of claim 11, wherein the fibrillation comprises atrial fibrillation.

13. The method of claim 1, wherein using the tissue map to plan one or more ablation paths comprises creating a route with optimized gap distances through which the ablation device moves.

14. The method of claim 1, wherein the tissue map comprises angles of the beam of energy relative to the target tissue, and wherein using the tissue map to adjust energy deliver settings comprises adjusting one or more of a frequency, voltage, duty cycle, power, and dwell time of the beam of ultrasound energy based on the angles.

15. The method of claim 1, wherein an area sensed by the single ultrasound transducer is identical to an area ablated by the single ultrasound transducer.

16. The method of claim 1, further comprising removing a noise profile component from the collected data to determine the gap distance.

* * * * *